United States Patent

Haslanger et al.

Patent Number: 4,588,743
Date of Patent: May 13, 1986

[54] 7-OXABICYCLOHEPTANE-SUBSTITUTED OXA PROSTAGLANDIN ANALOGS AND THEIR USE IN THE TREATMENT OF THROMBOLYTIC DISEASE

[75] Inventors: Martin F. Haslanger, Lambertville; Ravi K. Varma, Belle Mead; Steven E. Hall, Ewing Township, Mercer County, all of N.J.

[73] Assignee: E. R. Squibb & Sons, Inc., Princeton, N.J.

[21] Appl. No.: 693,647

[22] Filed: Jan. 22, 1985

[51] Int. Cl.$^4$ .................. A61K 31/34; C07D 307/00
[52] U.S. Cl. ........................................ 514/469; 549/463
[58] Field of Search ..................... 549/463; 514/469

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |

FOREIGN PATENT DOCUMENTS 0043292  8/1982  European Pat. Off.
2039909  8/1980  United Kingdom.

Primary Examiner—Henry R. Jiles
Assistant Examiner—Bernard I. Dentz
Attorney, Agent, or Firm—Lawrence S. Levinson; Burton Rodney

[57] ABSTRACT

7-Oxabicycloheptane substituted oxa prostaglandin analogs are provided having the structural formula

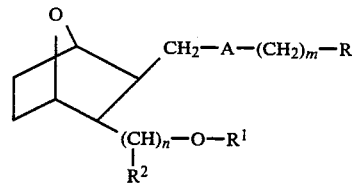

wherein R is OH,

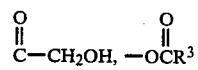

(wherein $R^3$ is lower alkyl, aryl, arylalkyl or lower alkylamino),

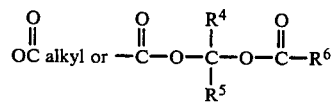

(wherein $R^4$ and $R^5$ are the same or different and can be H, alkyl, aryl or arylalkyl, and $R^6$ is alkyl or O-alkyl); $R^1$ is lower alkyl, aryl, aralkyl, cycloalkyl or cycloalkylalkyl; $R^2$ is hydrogen or lower alkyl; A is —CH=CH— or —(CH$_2$)$_2$—; n is 1 to 4, and m is 1 to 8, and including all stereoisomers thereof.

The compounds are cardiovascular agents useful, for example, in the treatment of thrombotic disease.

25 Claims, No Drawings

7-OXABICYCLOHEPTANE-SUBSTITUTED OXA PROSTAGLANDIN ANALOGS AND THEIR USE IN THE TREATMENT OF THROMBOLYTIC DISEASE

DESCRIPTION OF THE INVENTION

The present invention relates to 7-oxabicycloheptane oxa prostaglandin analogs which are cardiovascular agents useful, for example, in the treatment of thrombolytic disease. These compounds have the structural formula

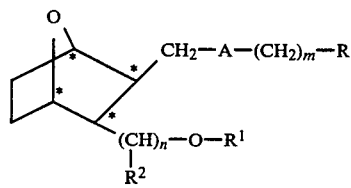

and including all stereoisomers thereof, wherein
A is CH=CH or $(CH_2)_2$; m is 1 to 8; R is

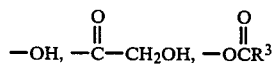

(wherein $R^3$ is lower alkyl, aryl, arylalkyl or aminoalkyl),

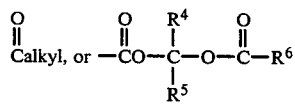

(wherein $R^4$ and $R^5$ may be the same or different and can be H, alkyl, aryl or arylalkyl and $R^6$ is alkyl, O-alkyl or aryl); n is 1 to 4; and $R^1$ is lower alkyl, aryl, arylalkyl, cycloalkyl or cycloalkylalkyl, and $R^2$ is H or lower alkyl, but where $R^2$ is lower alkyl, n is 1.

Thus, the compounds of formula I of the invention encompass five basic types of compounds which have the following structures:

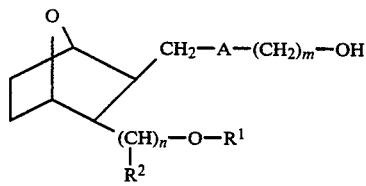

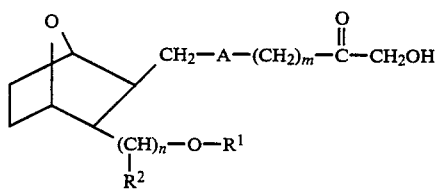

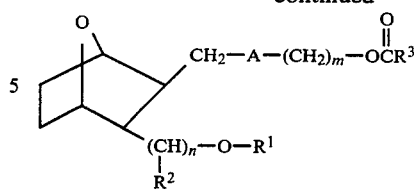

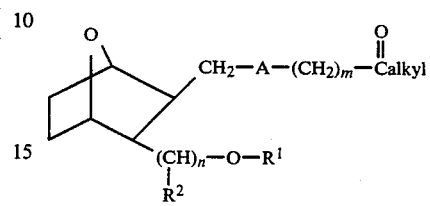

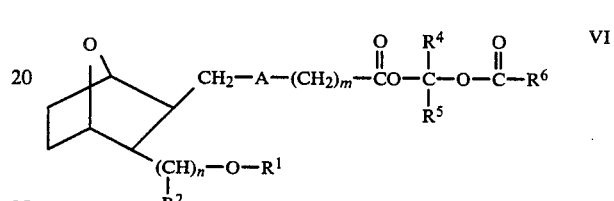

The term "lower alkyl" or "alkyl" by itself or as part of another group as employed herein includes both straight and branched chain radicals of up to 12 carbons, preferably 1 to 8 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an alkylthio substituent, an alkylamino substituent (e.g., $R^3NH-$ or $(R^3)_2N-$ wherein $R^3$ is lower alkyl), a haloaryl substituent, a cycloalkyl substituent (that is, cycloalkylalkyl) or an alkylcycloalkyl substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups.

The term "aryl" or "Ar" by itself or as part of another group as employed herein refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be lower alkyl, halogen (Cl, Br or F), or lower alkoxy.

The term "aralkyl", "aryl-alkyl" or "aryl-lower alkyl" by itself or as part of another group as used herein refers to lower alkyl groups as discussed above having an aryl substituent, such as benzyl.

The terms "$(CH_2)_m$" and "$(CH)_n$" include a straight or branched chain radical having from 1 to 8 carbons in the normal chain in the case of "$(CH_2)_m$" and 1 to 4 carbons in the normal chain in the case of "$(CH)_n$" and may contain one or more lower alkyl substituents. Examples of $(CH_2)_m$ groups and $(CH)_n$ groups (where appropriate) include $CH_2$,

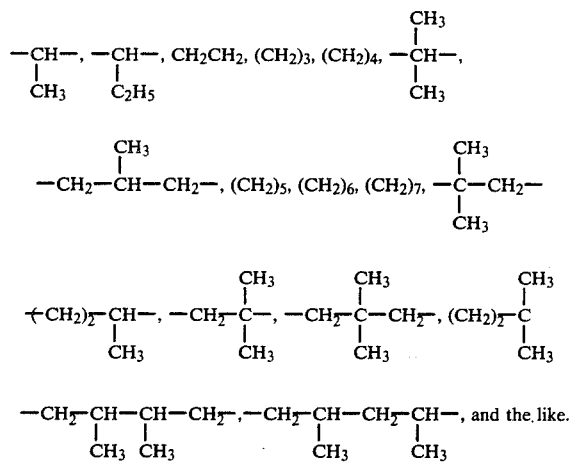
for NH₂ to
Preferred are those compounds of formula I wherein A is (CH₂)₂ or CH=CH, (CH₂)ₘ is
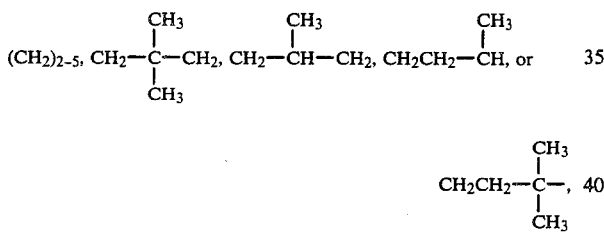
R is H, n is 1, 2 or 3, R¹ is pentyl, hexyl, cyclohexyl, cyclohexylmethyl, phenyl, benzyl, 2-phenylethyl or 3-phenylpropyl and R² is H, methyl or ethyl.
The various compounds of the invention may be prepared as outlined below.
A. Where n = 1, m is 1 and R is OH
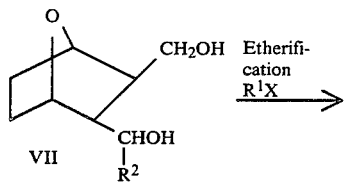
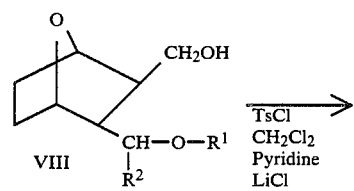
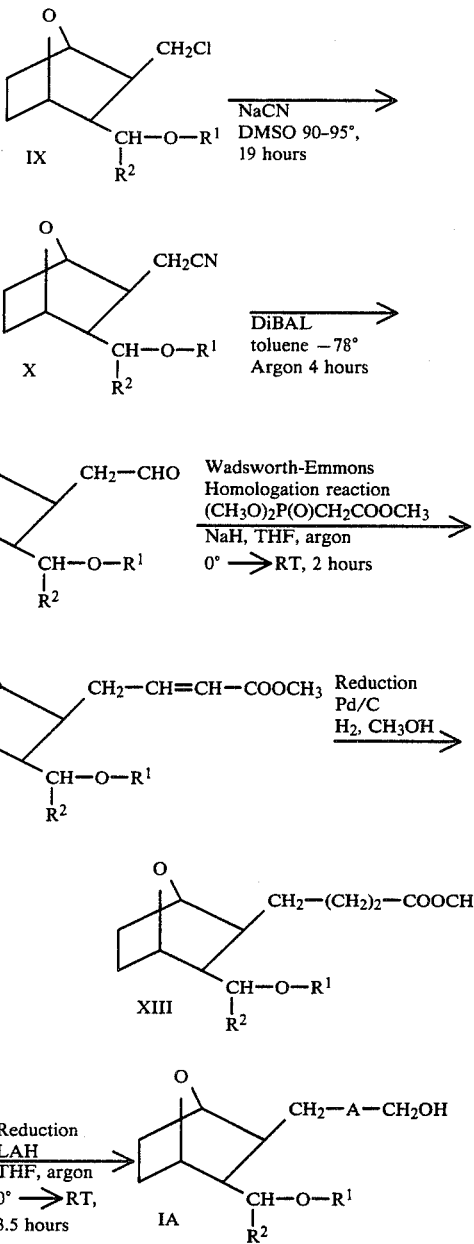
B. Where n = 1, m is >1, A is CH=CH and R is OH
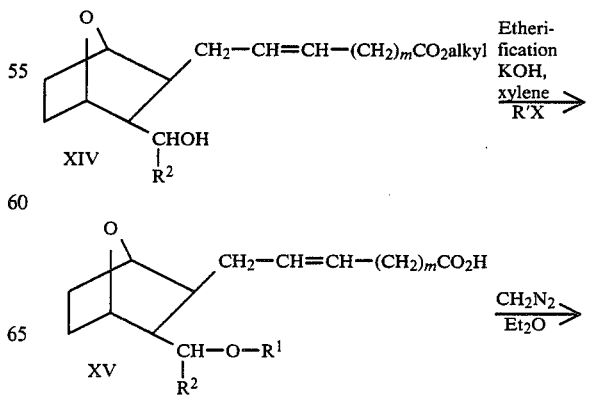

-continued
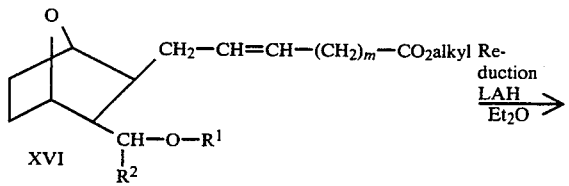
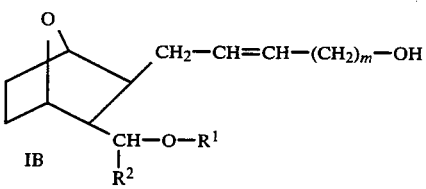
C. Where n = 1, m is >1, A is —(CH$_2$)$_2$— and R is OH
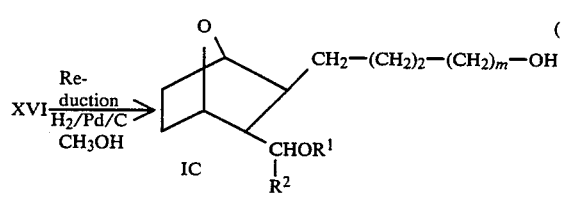   (1)
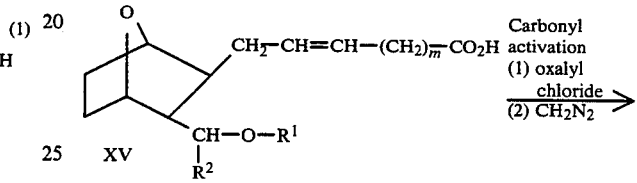
or
XIV $\xrightarrow{\text{Reduction}}_{\text{H}_2/\text{Pd/C}}$   (2)
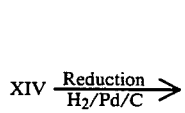
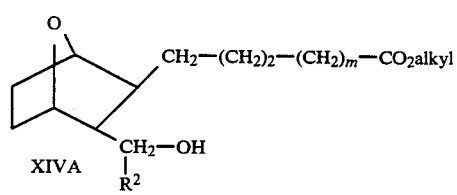
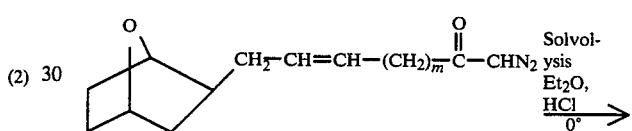
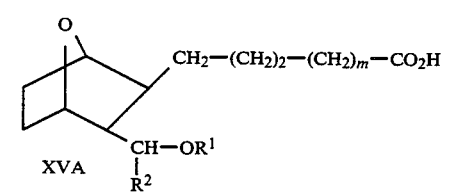
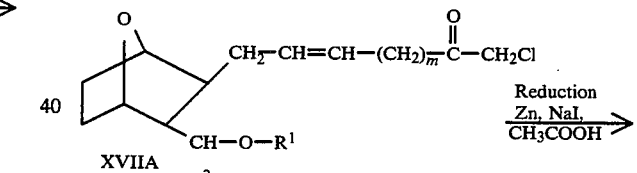
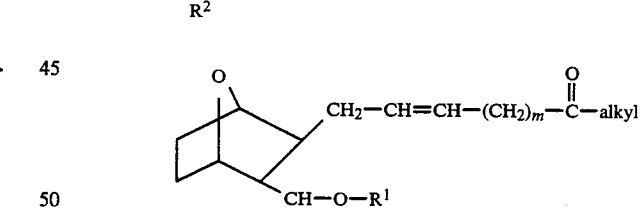
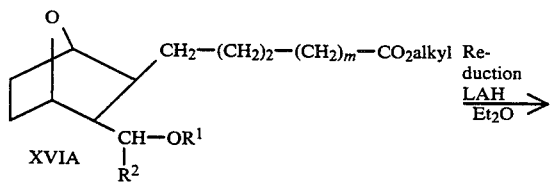
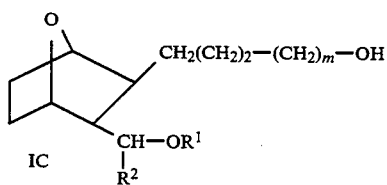
D. Where n = 1, m is 1 to 8, A is —CH═CH— and R is $\overset{O}{\overset{\|}{C}}$—alkyl
E. Where n is 1, m is 1 to 8, A is —(CH$_2$)$_2$— and R is $\overset{O}{\overset{\|}{C}}$—alkyl
XIV' $\xrightarrow{\text{Reduction}}_{\text{H}_2/\text{Pd/C}}$
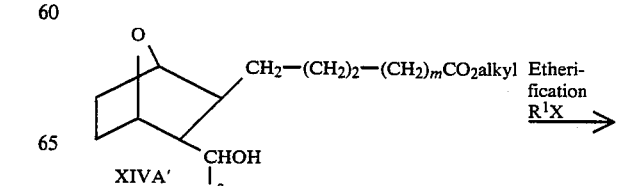

-continued

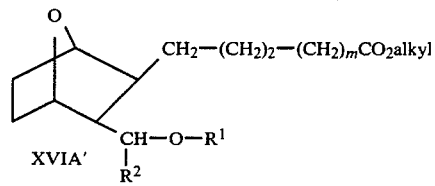

(where A is —(CH$_2$)$_2$—)

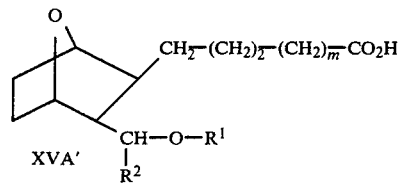

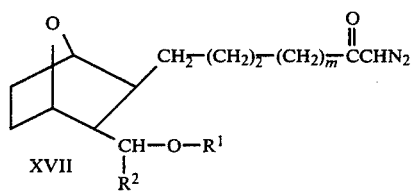

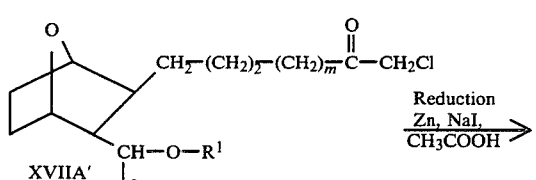

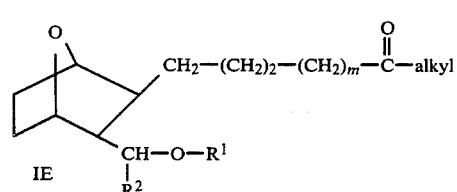

F. Where n = 1, A is CH=CH or (CH$_2$)$_2$, m is 1 to 8 and

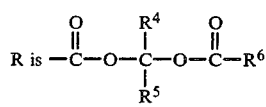

$$\begin{array}{c} XV' \\ \text{or} \\ XVA' \end{array} \xrightarrow[\text{(C}_2\text{H}_5)_3\text{N, NaI, DMF}]{\text{Esterification}}$$

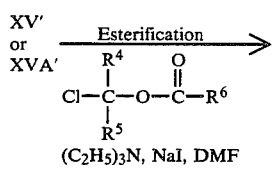

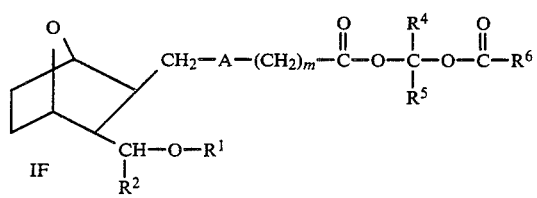

G. Where n = 1, A is CH=CH, and R is $\overset{O}{\overset{\|}{C}}$—CH$_2$—OH

-continued

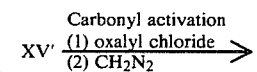

XV' $\xrightarrow[\text{(2) CH}_2\text{N}_2]{\text{Carbonyl activation}}$

[Structure XVII] $\xrightarrow[\text{Cu(OAc)}_2, 90\text{-}95°]{\begin{array}{c}\text{Displacement with acetate dioxane, acetic acid}\end{array}}$

[Structure XVIII] $\xrightarrow[\text{K}_2\text{CO}_3]{\text{Solvolysis}}$

[Structure IG]

H. Where n = 1, A is (CH$_2$)$_2$ and R is $\overset{O}{\overset{\|}{C}}$—CH$_2$OH XVIII $\xrightarrow[\text{H}_2, \text{CH}_3\text{OH}]{\text{Reduction Pd/C}}$

[Structure XIX] $\xrightarrow[\text{K}_2\text{CO}_3]{\begin{array}{c}\text{Solvolysis}\\\text{CH}_3\text{OH}\end{array}}$

[Structure IH]

I. Where n is 1, R is —O$\overset{O}{\overset{\|}{C}}$—R$^3$

[Structure IA, IB, IC] $\xrightarrow[\text{(HO—C—R}^4\text{—NH—Pro)}]{\text{Acylation or Protected amino acid (DCC, DMAP)}}$

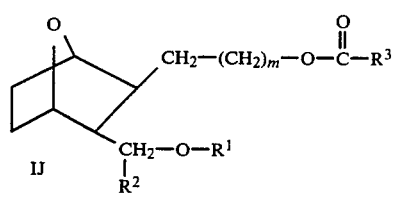
IJ

J. Where n is 2 to 4 - to prepare starting materials:

XIV
or
XIVA   Collins
or     oxidation
XIV'
or
XIVA'

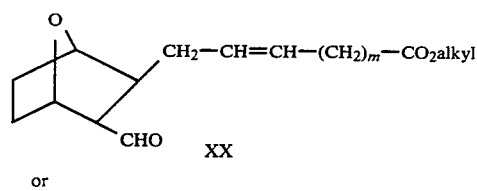
XX or

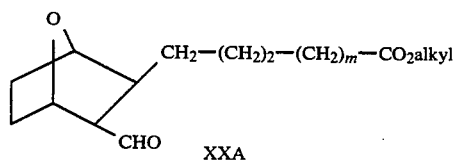
XXA $$\xrightarrow[(C_6H_5)_3P=CHOCH_3]{\text{Wittig}}$$

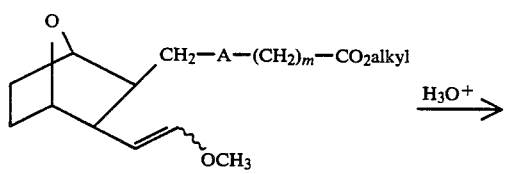
XXI or XXIA $\xrightarrow{H_3O^+}$

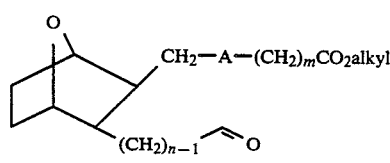
(repeat n−1 times)

XXII (where A is —CH=CH—)
or
XXIIA (where A is —(CH$_2$)$_2$—)

XXII
or     $\xrightarrow[NaBH_4]{\text{Reduction}}$
XXIIA

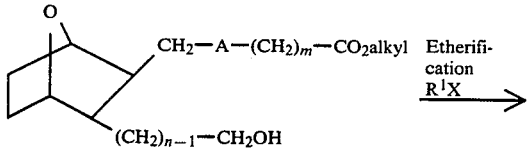   Etherification $\xrightarrow{R^1X}$

XXIII (where A is —CH=CH—)
or
XXIIIA (where A is —(CH$_2$)$_2$—)

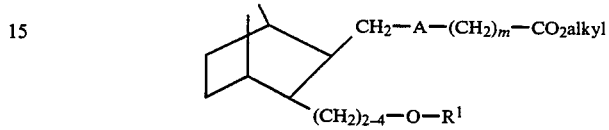

XXIV (where A is —CH=CH—)
or
XXIVA (where A is —(CH$_2$)$_2$—)

Compounds of the invention wherein R is OH, m is 1, and n is 1, that is

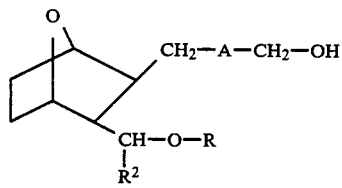 IA may be prepared as outlined in reaction sequence "A".
Diol compound VII is employed as the starting material and is prepared by reacting the mesoanhydride A

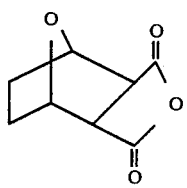 A (prepared as described in U.S. Pat. Nos. 4,143,054 and 4,220,594) with a reducing agent such as lithium aluminum hydride or diisobutylaluminum hydride in the presence of an inert organic solvent such as tetrahydrofuran, toluene or ether.

Diol VII is etherified by reaction with a strong base such as sodium hydride in the presence of an inert solvent such as dimethylformamide and a compound of the structure B

R$^1$X                              B (wherein X is Br, Cl, OSO$_2$CH$_3$ or OSO$_2$—⟨C$_6$H$_4$⟩—CH$_3$)

at temperatures of from about 50° to about 110° C., to form the ether VIII. Ether VIII is next chlorinated by reacting with p-toluenesulfonyl chloride, lithium chloride and organic base such as pyridine to form IX. Compound IX is then reacted with sodium cyanide, in the presence of an inert solvent such as dimethylsulfoxide or dimethylformamide at 90° to 95° C. for 2 to 24 hours, to form cyanide compound X. Cyanide compound X is then treated with diisobutylaluminum hydride (DiBAL) at reduced temperatures of from about −78° to about −20° C. under an inert atmosphere, such as argon, to form the aldehyde XI. The aldehyde XI is then subjected to a Wadsworth-Emmons homologation reaction wherein XI is treated with a phosphorus compound C

$(CH_3O)_2P(O)CH_2COOCH_3$     (C)

in the presence of strong base such as sodium hydride and an inert solvent such as tetrahydrofuran under an inert atmosphere, such as argon, to form ester XII

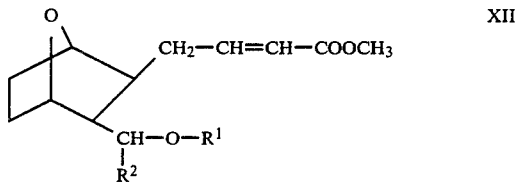

wherein A in the final product is to be CH=CH, compound XII is reduced by treatment with lithium aluminum hydride in the presence of an inert solvent such as tetrahydrofuran under an inert atmosphere such as argon to form compound IA wherein A is CH=CH.

Compounds of formula IA wherein A is $(CH_2)_2$, m is 1, n is 1 and R is OH are prepared as shown in the reaction sequence "A" wherein compound X is reduced by reaction with hydrogen in the presence of palladium on charcoal or similar catalyst to form compound XIII which is then reduced by treatment with lithium aluminum hydride as described above to form compound IA wherein A is $(CH_2)_2$.

In the reaction sequences identified as "B" and "C", where in Formula I n is 1, m is greater than 1, A is CH=CH and R is OH, the lower alkyl ester containing the hydroxymethyl group, that is, compound XIV (where A is —CH=CH—, reaction sequence "B") or XIVA (where A is —$(CH_2)_2$, reaction sequence "C") (prepared as described in U.S. Pat. No. 4,143,054) is employed as the starting material. Thus, where A is —CH=CH—, compound XIV is subjected to an etherification reaction, for example, by reacting with compound B of the structure $R^1X$     B

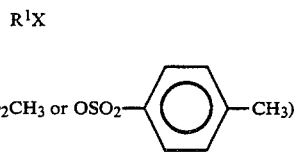

(wherein X is Cl, Br, I, $OSO_2CH_3$ or $OSO_2$—⟨phenyl⟩—$CH_3$)

in the presence of a strong inorganic base such as KOH or NaOH, and an appropriate solvent to form acid XV which is treated with diazomethane and ethyl ether to form ester XVI. To form the ester XVA (where A is $(CH_2)_2$), (Reaction sequence "C"), compound XIV is reduced, for example with hydrogen over a palladium on carbon catalyst, to form hydroxymethyl compound XIVA (where A is $(CH_2)_2$) and compound XIVA is subjected to an etherification reaction as described above to form acid XVA (where A is $(CH_2)_2$). Thereafter, acid XV or XVA is treated with diazomethane and ethyl ether to form ester XVI or XVIA. Ester XVI or XVIA may then be reduced by reaction with lithium aluminum hydride as described above to form compound IB or IC, respectively.

Alternatively, ester XVI may be simply reduced by treating XVI with hydrogen in the presence of palladium on charcoal catalyst to form compound IC.

In carrying out the above reactions, the hydroxymethyl compound XIV or XIVA is employed in a molar ratio to the compound B, that is, XIV or XIVA:B, of within the range of from about 0.8:1 to about 1:5, employing a solvent such as xylene, tetrahydrofuran (THF), dimethylsulfoxide (DMSO) or dimethylformamide (DMF).

Where in $R^1X$, X is Br or Cl, a phase transfer etherification is employed in which case THF is used as the solvent and a phase transfer reagent such as $Bu_4N$-$HSO_4$, or $(C_6H_5CH_2)(CH_3)_3NHSO_4$ is employed.

The starting alcohol XIV wherein $R^2$ is lower alkyl may be prepared by reacting the aldehyde D

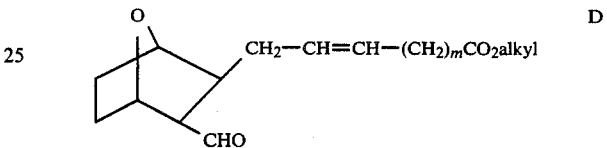

prepared as described in U.S. Pat. No. 4,143,054 with an alkyl Mg halide E of the structure $R^2MgX$ (wherein X is Cl or Br)     (E)

at reduced temperatures of less than about 0° C. in the presence of an inert organic solvent such as tetrahydrofuran.

In the reaction sequences identified as "D" and "E", where in Formula I n is 1, the lower alkyl ester containing the hydroxymethyl group, that is, compound XIV' (where A is —CH=CH—, reaction sequence "D") or XIVA' (where A is —$(CH_2)_2$, reaction sequence "E") (prepared as described in U.S. Pat. No. 4,143,054) is employed as the starting material. Thus, where A is —CH=CH—, compound XIV' is subjected to an etherification reaction, for example, by reacting a compound of the structure $R^1X$     B

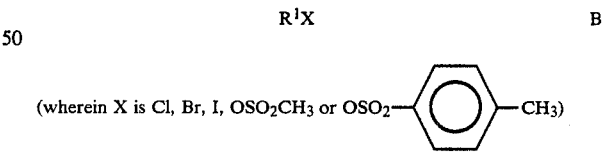

(wherein X is Cl, Br, I, $OSO_2CH_3$ or $OSO_2$—⟨phenyl⟩—$CH_3$)

in the presence of a strong inorganic base such as KOH or NaOH, and an appropriate solvent to form ester XVI'. To form the ester XVIA' (where A is $(CH_2)_2$), (Reaction sequence "E"), compound XIV' is reduced, for example with hydrogen over a palladium on carbon catalyst, to form hydroxymethyl compound XIVA' (where A is $CH_2)_2$) and compound XIVA' is subjected to an etherification reaction as described above to form ester XVIA' (where A is $(CH_2)_2$). In carrying out the above reaction, the hydroxymethyl compound XIV' or XIVA' is employed in a molar ratio to the halide B, that is, XIV or XIVA':A of within the range of from about 0.8:1 to about 1:5, employing a solvent such as xylene, tetrahydrofuran (THF), dimethylsulfoxide (DMSO) or dimethylformamide (DMF).

Where in R¹X, X is Br or Cl, a phase transfer etherification is employed in which case THF is used as the solvent and a phase transfer reagent such as Bu₄N-HSO₄, or (C₆H₅CH₂)(CH₃)₃)NHSO₄ is employed.

The ester XVI' or XVIA' is hydrolyzed to the corresponding acid XV or XVA' which is subjected to a carbonyl activation reaction by reacting XV' or XVA' with oxalyl chloride and diazomethane to form diazo compound XVII or XVII' which is subjected to solvolysis by treatment with ethyl ether and hydrochloric acid at reduced temperature to form chloro ketone XVIIA or XVIIA' which in turn is reduced by reaction with acetic acid in the presence of zinc and sodium iodide to form the compounds of the invention ID or IE.

Referring to sequence "F", compounds of the invention wherein R is

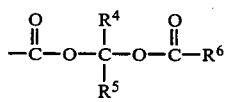

may be prepared by esterifying acid XV' or XVA' by reaction with a compound of the structure F

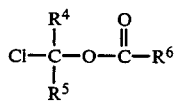   F in the presence of base such as triethylamine, NaI and dimethylformamide to form compound of the invention IF.

Referring now to reaction sequence "G", compounds of formula I where n is 1, A is CH=CH and R is

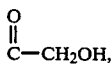

that is IG, may be prepared by subjecting compound XVI' to a carbonyl activation reaction by reacting XV' with oxalyl chloride and diazomethane to form XVII, treating XVII with acetic acid and dioxane in the presence of copper acetate to form the acetate XVIII which is then subjected to solvolysis by treating with methanol and potassium carbonate to form compound IG.

As seen in reaction sequence "H", compounds of formula I wherein n is 1, A is (CH₂)₂ and R is

that is compound IH, may be prepared by reducing acetate XVIII by treating with hydrogen in the presence of a palladium on carbon catalyst to form acetate XIX which is then subjected to solvolysis as described above with respect to XVIII to form compound IH.

Referring now to reaction sequence "I", compounds wherein n is 1 and R is

wherein R³ is alkyl, that is compound IJ, may be prepared by subjecting alcohol IA, IB or IC to acylation by reacting IA, IB or IC with the appropriate acid anhydride in the presence of an organic base such as pyridine.

Compounds of formula IJ wherein R³ is aminoalkyl, such as

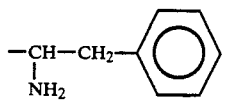

may be prepared by reacting alcohol IA, IB or IC with a protected amino acid of the structure G

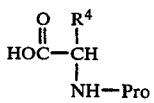   G wherein R⁴ is lower alkyl or arylalkyl, and the protecting group (Pro) may be t-butyloxycarbonyl, or other conventional protecting group, in the presence of dicyclohexyldicarbodiimide and dimethylaminopyridine to form the protected compound H

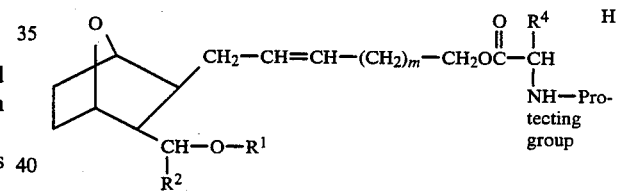

The protecting group is then removed by conventional methods, such as trifluoroacetic acid in the presence of methylene chloride, to form compound IJ'

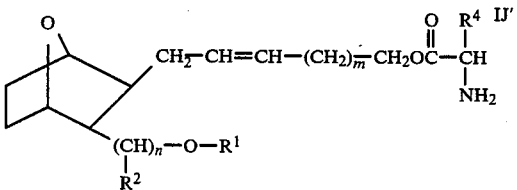

Compound IJ' may be reduced by treatment with H₂ in the presence of Pd/C to form IJ''

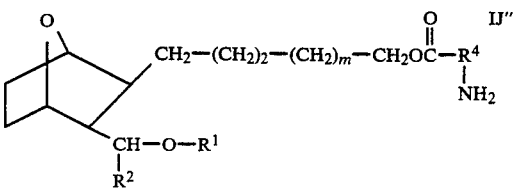

Compounds of formula IJ wherein R³ is aryl may be prepared by acylation of the alcohol IA with the requisite acid chloride or anhydride under standard conditions.

In the reaction sequence identified as "J", where in Formula I n is 2 to 4, the starting lower alkyl ester containing the hydroxymethyl group, that is, compound XIV, XIVA, XIV' or XIVA', (prepared as described in U.S. Pat. No. 4,143,054) is used to form the aldehyde XX (where A is —CH=CH—) or XXA (where A is —(CH$_2$)$_2$). Thus, to form aldehyde XX where A is —CH=CH—, compound XIV is subjected to a Collins oxidation, for example, by reacting XIV with chromium trioxide in pyridine. To form the aldehyde XXA (where A is (CH$_2$)$_2$), compound XIV is reduced, for example with hydrogen over a palladium on carbon catalyst, to form hydroxymethyl compound XIVA (where A is (CH$_2$)$_2$) and compound XIVA is subjected to a Collins oxidation to form aldehyde XXA (where A is (CH$_2$)$_2$).

The aldehyde XX or XXA is used to prepare aldehyde XXII or XXIIA (where n is 2–4) by carrying out a homologation sequence, such as a Wittig reaction with (C$_6$H$_5$)$_3$P=CHOMe followed by hydrolysis, (n−1) times. The aldehyde XXII or XXIIA (where n is 2–4) is thus carried on to compounds of this invention where n is 2–4, by reducing aldehyde XXII or XXIIA employing a reducing agent such as sodium borohydride or sodium cyanoborohydride in a solvent such as methanol to form the alcohol ester XXIII or XXIIIA which is subjected to an etherification reaction as described above to form XXIV or XXIVA. The ester XXIV or XXIVA may then be used to prepare compounds of the invention employing techniques as described herein for starting esters wherein n is 1.

Compounds of Formula I wherein R$^1$ is aryl such as phenyl or substituted phenyl may be prepared by reacting the alcohol XIV or XIVA or XXIII or XXIIIA with triphenylphosphine and diethylazodicarboxylate in solution with an inert solvent such as THF, and thereafter without isolating any products, reacting the above reaction mixture with an aryl alcohol wherein the hydroxy group is directly attached to the aromatic ring, such as phenol or a substituted phenol, under an inert atmosphere, such as argon or nitrogen, to form the ester of the structure

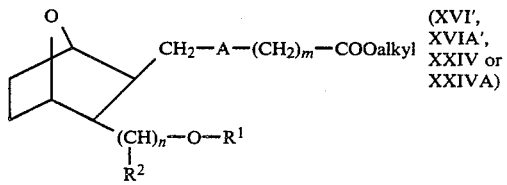
(XVI', XVIA', XXIV or XXIVA)

wherein R$^1$ is phenyl or substituted phenyl which is then used to prepare compounds of the invention as described hereinbefore.

The starting alcohol XIV or XIV' wherein

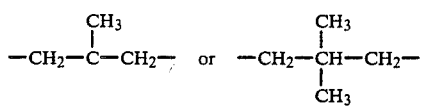

prepared as described in U.S. Pat. No. 4,143,054 or alternatively by subjecting the hemiacetal J

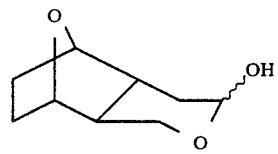

to a Wittig reaction by treating hemiacetal J with the reaction product of a carboxyalkyltriphenylphosphonium bromide K $$Br^-(C_6H_5)_3P^+CH_2(CH_2)_{m'}COOH \qquad (K)$$

wherein (CH$_2$)$_{m'}$ is

and potassium t-amylate and subsequently with diazomethane to form the alcohol XIVB

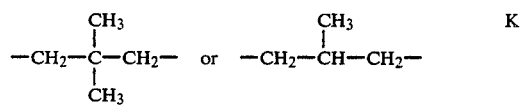

Intermediates wherein (CH$_2$)$_m$ is

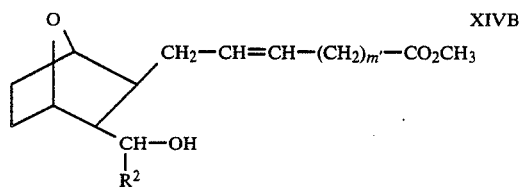

wherein x is 1 to 7) may be prepared by simply reacting an ester XXVII of the structure

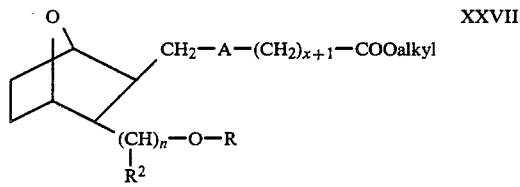

prepared as described hereinbefore with lithium diisopropylamine and then treating the reaction with hexamethylphosphorous amide and an alkyl halide L at reduced temperatures alkyl-Hal                    (L)

wherein Hal is I, Br, or Cl
to form the ester XXVIII

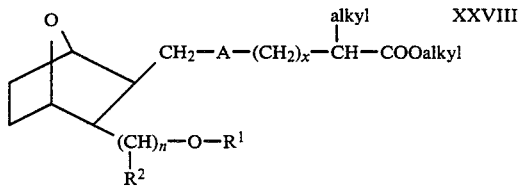

(wherein the above alkyls may be the same or different)

Intermediates wherein $(CH_2)_m$ is

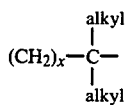

(wherein x is 1 to 7) may be prepared by reacting ester XXVIII with lithium diisopropylamine and then treating the reaction with an alkyl halide L at reduced temperatures to form the ester XXIX

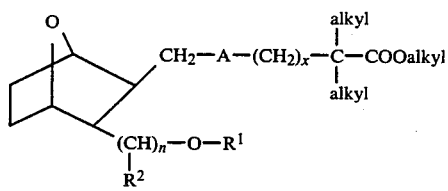
XXIX (wherein the various alkyls may be the same or different)

The esters XIVB, XXVII, XXVIII and XXIX may be employed as intermediates in making the compounds of the invention employing techniques set out below with respect to compounds wherein $(CH_2)_m$ does not include ay alkyl substitutents.

The compounds of this invention have four centers of asymmetry as indicated by the asterisks in formula I. However, it will be apparent that each of the formulae set out above which does not include asterisks still represents all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

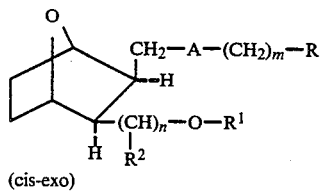
Ie
(cis-exo)

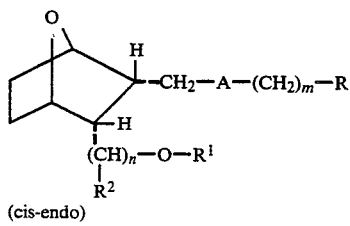
If
(cis-endo)

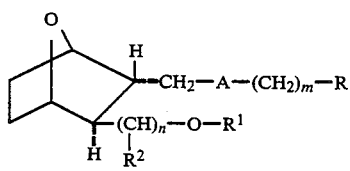
Ig

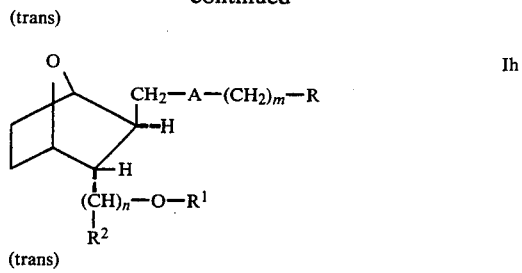
Ih
(trans)

The nucleus in each of the compounds of the invention is depicted as

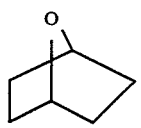

for matter of convenience; it will also be appreciated that the nucleus in the compounds of the invention may be depicted as

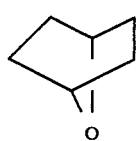

The compounds of this invention are cardiovascular agents useful as platelet aggregation inhibitors, such as in inhibiting arachidonic acid induced platelet aggregation, e.g., for treatment of thrombolytic disease, such as coronary or cerebral thromboses or in inhibiting bronchoconstriction, such as associated with asthma. They are also selective thromboxane $A_2$ receptor antagonists and synthetase inhibitors, e.g., having a vasodilatory effect for treatment of myocardial ischemic disease, such as angina pectoris. The compounds of the invention are also arachidonic acid cyclooxygenase inhibitors. In addition, the compounds of the invention are useful as analgesic agents in the manner of aspirin and indomethacin as indicated by reaction thresholds to pressure in edematous hindpaws [Ref: Winter et al, J. Pharmacol, Exp. Ther. 150:165, 1965] and as antiinflammatory agents in mammals, as indicated by carrageenin-induced edema in the rat [Ref: Winter et al., J. Pharmacol., Exp., Ther. 141:369, 1963]. They may be used to decrease joint swelling, tenderness, pain and stiffness in conditions such as rheumatoid arthritis.

The compounds of this invention when used in combination with a cyclic AMP phosphodiesterase inhibitor, such as theophylline or papaverine, may be used in the preparation and to prolong storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

($1\alpha,2\beta,3\beta,4\alpha$)-4-[3-[(Hexyloxy)methyl]-7-oxabicyclo[2.2.1]hept-2-yl]butanol A. ($1\alpha,2\beta,3\beta,4\alpha$)-cis-exo-7-oxabicyclo[2.2.1]heptane-2,3-dimethanol To a suspension of 11.4 g lithium aluminum hydride (300 mmole, 1.6 eq.) in 400 ml of dry THF at 0° C. was added dropwise a solution of 32 g cis-exo-hexahydro-4,7-epoxyisobenzofuran-1,3-dione (mesoanhydride) (190 mmole) in 400 ml of dry THF over a period of 1 hour. The reaction mixture was stirred at 25° C. for 18 hours, cooled to 0° C. and quenched by slow addition of a saturated $Na_2SO_4$ solution, and filtered. The solid was washed with three 100 ml portions of $CH_2Cl_2$. The combined organic layer was dried over $MgSO_4$ and concentrated to give 32 g of title diol as a colorless solid.

B. ($1\alpha,2\beta,3\beta,4\alpha$)-3-[(Hexyloxy)methyl]-7-oxabicyclo[2.2.1]heptane-2-methanol A suspension of 50% sodium hydride (16.7 g or 0.35 mole; prewashed with ether) in dry dimethylformamide (350 ml) was cooled down to 0° under $N_2$ and treated dropwise with a solution of the Part A diol (50 g; 0.316 mole) in dry dimethylformamide (150 ml). The reaction mixture was stirred at 0° for 30 minutes and at room temperature for 30 minutes after which n-hexylbromide (59.8 ml of 70.3 g; 0.42 mmole of 1.33 eq.) was added. The mixture was then stirred at room temperature for 15 minutes, at 120° (oil bath) for 15 hours, cooled and quenched with 25% ammonium chloride solution (300 ml). The resulting suspension was extracted 3 times with ether (1.0 liter), the organic extracts were dried (anhydrous $MgSO_4$), filtered and evaporated to a syrup. Yield: 90.0 g.

The crude product mixture was chromatographed (gravity) on a silica gel column (Woelm; 1.2 kg), eluting the column with EtoAc-hexane (1:4, 24.3 liters). The desired fractions were combined and evaporated to give 26.94 g of homogeneous (tlc) compound. An additional 28.7 g of the title alcohol compound containing a trace of another component was obtained from other fractions giving a total yield of 72.6%. An analytical sample was obtained by distilling 1.0 g of material on a Buchi GKR-50 apparatus. (Temperature 225°; 0.4 mm).

$^1$H-NMR (270 MHz, $CDCl_3$): $\delta$ 0.89 (t, 3H, J= ~8, $H_{21}$); 1.29-1.7 (m, 12H); 2.2 (m, 2H, J=18 4.0, $H_8+H_{13}$); 3.3-3.80 (m, 7H, —, $H_7$, $H_{14}+H_{16}$); 4.23 (d, 1H, J= ~4.0, $H_9$); 4.29 (d, 1H, J= ~4.0, $H_{12}$).

Anal. Calcd. for $C_{14}H_{26}O_3$: C, 69.38; H, 10.81%. Found: C, 69.36; H, 10.60%.

C. ($1\alpha,2\beta,3\beta,4\alpha$)-3-[(Hexyloxy)methyl]-7-oxabicyclo[2.2.1]heptane-2-methylchloride 5.0 g (20.6 mole) of ($1\alpha$, $2\beta$, $3\beta$, $4\alpha$)-3-(hexyloxy)-methyl-7-oxabicyclo[2.2.1]-heptane-2-methanol (from Part B), 4.73 g (24.8 mmole of 1.2 eq.) of p-toluenesulfonylchloride, 873 mg (20.6 mmole) of lithium chloride and 3.3 ml of dry pyridine were stirred together in dichloromethane (15 ml) at room temperature under nitrogen for 24 hours. The reaction mixture was partitioned between ether (250 ml) and saturated sodium chloride solution (20 ml). The aqueous phase was re-extracted with ether (250 ml), the combined organic extracts were dried (anhydrous $MgSO_4$), filtered and the clear filtrate was evaporated down to a syrup. Yield: 5.3 g.

The crude product mixture was flash chromatographed on a silica gel column (LPS-1), eluting the column with $Et_2O$:hexane (1:9, 6.0 liters) and $Et_2O$:hexane (1:1; 6.0 liters). The fractions containing the desired product were combined and evaporated down to give 3.35 g (62.4%) of the title compound as a homogeneous (tlc) oil with consistent $H^1$ and $C^{13}$ spectral data.

D. ($1\alpha,2\beta,3\beta,4\alpha$)-3-[(Hexyloxy)methyl]-7-oxabicyclo[2.2.1]heptane-2-acetonitrile A solution of Part C chloro compound (3.35 g; 12.8 mmole) and sodium cyanide (1.29 g; 2.05 eq.) in dry dimethylsulfoxide (4.6 ml) was heated at 90°-95° (oil bath) under argon for 19 hours with stirring. The mixture was cooled to room temperature, diluted with water (12 ml) and extracted twice with ether (75 ml). The organic extracts were dried (anhydrous $MgSO_4$), filtered and the clear filtrate concentrated in vacuo to a light yellow oil (3.18 g).

This oil was flash chromatographed on a silica gel column (LPS-1), eluting the column with $Et_2O$:hexane (1:2, 7.5 liters). The desired fractions were combined and concentrated to give 3.06 g (95%) of the title cyano compound as a homogeneous (tlc) light yellow oil with consistent $H^1$ and $C^{13}$-NMR spectral data.

E. ($1\alpha,2\beta,3\beta,4\alpha$)-3-[(Hexyloxy)methyl]-7-oxabicyclo[2.2.1]heptane-2-acetaldehyde 1.5 g (5.97 mmole) of the Part D cyano compound was dissolved in dry toluene (7.0 ml), cooled, stirred in a bath at $-78°$ (dry ice-acetone) under argon, and treated dropwise with 5.4 ml of diisobutylaluminum hydride (25% by wt. in toluene; 9.49 mmole or 1.5 eq.). After 4.0 hours, the mixture was quenched at $-78°$ with 25% $NH_4Cl$ (6.0 ml), stirred for 30 minutes, warmed to about 0°, acidified with 1N HCl (16 ml), and stirred for about 30 minutes. The mixture was then extracted twice with dichloromethane (50 ml), the organic extracts were washed with saturated sodium chloride solution (20 ml), dried (anhydrous $MgSO_4$), filtered and concentrated in vacuo to give 1.45 g (95.4%) of the title aldehyde as a homogeneous (tlc) yellow oil with consistent $H^1$ and $C^{13}$-NMR spectral data.

F. [$1\alpha,2\beta(2E),3\beta,4\alpha$]-4-[3-[(Hexyloxy)methyl]-7-oxabicyclo[2.2.1]hept-2-yl]-2-butenoic acid, methyl ester 420 mg (8.75 mmole) of 50% NaH on paraffin was suspended in dry distilled tetrahydrofuran (60 ml), cooled down to 0° under argon and was treated dropwise with trimethylphosphonoacetate (2 ml; 12.4 mmole). The thick slurry was stirred at 0° for 30 minutes, room temperature for 1 hour and cooled back down to 0°. It was then treated dropwise with a solution of Part E aldehyde (2.0 g; 7.86 mmole) in tetrahydrofuran (20 ml). The mixture was stirred at 0° for 30 minutes, room temperature for 2 hours and was then acidified with glacial acetic acid (2.0 ml). It was then stirred for 30 minutes, evaporated to dryness in vacuo and the resulting solid was partitioned twice between saturated NaHCO$_3$ solution (100 ml) and ether (400 ml). The organic phase was washed with water (200 ml), dried (anhydrous MgSO$_4$), filtered through a bed of silica gel (Baker; 30 ml) and was evaporated to dryness to give 2.48 g (100%) of title ester compound as an oil with a consistent $^{13}$C NMR spectrum.

G. [1α,2β,3β,4α]-4-[3-[(Hexyloxy)methyl]-7-oxabicyclo[2.2.1]hept-2-yl]butanoic acid, methyl ester 2.48 g (7.86 mmole) of Part F title ester compound was dissolved in dry methanol (140 ml) and hydrogenated at atmospheric pressure, at room temperature, in the presence of 5% Pd/C (420 mg) for 3 to 4 hours. The suspension was filtered and concentrated to a homogeneous (TLC) oil (2.49; 96.6%) with a consistent $^{13}$C spectrum which showed the absence of the double bond.

H. (1α,2β,3β,4α)-4-[3-[(Hexyloxy)methyl]-7-oxabicyclo[2.2.1]hept-2-yl]butanol

A solution of Part G reduced ester compound (2.1 g; 6.72 mmole) in dry tetrahydrofuran (10 ml) was added dropwise to a suspension of lithium aluminum hydride (420 mg; 11.1 mmole) in dry tetrahydrofuran (50 ml) at 0° under argon. The reaction mixture was stirred at 0° for 30 minutes, room temperature for 3 hours, and quenched by the successive addition of water (0.42 ml), 10% NaOH (0.7 ml) and water (1.26 ml). The granular precipitates were filtered off and washed with small amounts of ether. The filtrate was diluted with ether (300 ml), dried (anhydrous MgSO$_4$), filtered and was concentrated to give a homogeneous (TLC) oil (1.9 g; 100%). The product (1.4 g) was chromatographed (flash) on a silica gel column (LPS-1), eluting with Et$_2$O:hexane (1:1, 1.5 liters) and Et$_2$O:hexane (3:1, 2.0 liters) to give, after drying in vacuo, the analytical specimen of the title product as a clear oil (1.25 g) with consistent mass, H$^1$-NMR, C$^{13}$-NMR and IR spectral data.

Anal. Calcd. for C$_{17}$H$_{32}$O$_3$: C, 71.79; H, 11.34%. Found: C, 71.56; H, 11.29%.

$^1$H-NMR (270 MHz, CDCl$_3$): δ 0.91 (t, 3H, J=18 9; H$_{21}$); 1.2–2.09 (m, 21H, —, —); 3.25–3.42 (m, 4H, —, H$_{14}$+H$_{16}$); 3.63 (t, 2H, J=~6, H$_4$); 4.28 (d, 1H, J=~4, H); 4.40 (d, 1H, J=18 4, H$_{12}$).

EXAMPLE 2

[1R-[1α,2β(5Z),3β,4α]]-7-[3-[(Hexyloxy)methyl]-7-oxabicyclo[2.2.1]hept-2-yl]-2,2-dimethyl-5-hepten-1-ol A. [1R-[1α,2β(Z),3β,4α]]-7-[3-[(Hexyloxy)methyl]-7-oxabicyclo[2.2.1]hept-2-yl]-5-heptenoic acid, methyl ester (1) [3aR-[1-(1R,2S,5R),3aα,4α,7α, 7aα]]-Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No. 4,143,054 (21 g, 0.13 mole), levo-menthol (20.2 g, 0.13 mole) and p-toluenesulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,—-7α,7aα]]-octahydro-1-[[5-methyl-2-(1-methylethyl)cyclohexyl]oxy]-4,7-epoxyisobenzofuran, m.p. 109°–111° C.

(2) [3aS-(3aα, 4α, 7α, 7aα)]-Octahydro-1-benzyloxy-4,7-epoxyisobenzofuran

A solution of [3aR-[1-(1R,2S,5R),3aα,4α,—7α,7aα]]-octahydro-1-[[5-methyl-2-(1-methylethyl)cyclohexyl]oxy]-4,7-epoxy-isobenzofuran (from Part (1)) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1) R$_f$=0.25; vanillin spray and heat.

(3) [3aS-(3aα,4α,7α,7aα)]-Octahydro-4,7-epoxyisobenzofuran-1-ol

A mixture of title (2) compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C. [α]$_D$=−44° [α]$^{Hg}_{365}$=−122° (c=10 mg/ml, MeOH).

TLC: silica gel; ethyl acetate/dichloromethane (1:1), R$_f$=0.2; vanillin spray and heat.

(4) [1R-(1α,2β,3β,4α)]-3-(Hydroxymethyl)-2-(2-methoxyethenyl)-7-oxabicyclo[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title (3) compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title product contaminated with phosphine oxide. This product was distilled in vacuo to yield 3 g of title compound, b.p. 90° C./0.01 mm.

[α]$_D$=+44° [α]$^{Hg}_{365}$=+138° (c=11 mg/ml, MeOH)

TLC: silica gel; ethyl acetate/dichloromethane (1:1); R$_f$=0.2; vanillin spray and heat.

(5) [4aS-(4aα,5α,8α,8aα)]-Octahydro-5,8-epoxy-(1H)-benzopyran-3-ol

A solution of title (4) compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title compound, m.p. 104°–105° C.

$[\alpha]_D = -27.2°$ $[\alpha]^{Hg}_{365} = 0°$ (c=7.9 mg/ml, MeOH)

(6) [1R-[1α,2β(5Z),3β,4α]]-7-[3-Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title (5) compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$ $[\alpha]^{Hg}_{365} = 0°$ (c=16.9 mg/ml MeOH)

TLC: silica gel; ether; $R_f = 0.4$; vanillin spray and heat.

(7) [1R-[1α,2β(Z),3β,4α]]-7-[3-[(Hexyloxy)methyl]-7-oxabicyclo[2.2.1]hept-2-yl]-5-heptenoic acid Dry xylene (80 ml) containing powdered KOH (2.0 g, 35 mmole) was distilled under stirring to remove ~40 ml of xylene. A solution of optically active alcohol from Part (6) (1.073 g, 4.0 mmole) in dry xylene (20 ml) was then added and the distillation was continued to remove another 20 ml of xylene. A solution of n-hexylmesylate (3.6 g, 20 mmole) in xylene (10 ml) was then added resulting in a moderately exothermic reaction. A jelly-like deposit soon started to appear. After 1.5 hours, the mixture was cooled, diluted with CH₂Cl₂ (100 ml) and water (100 ml) and was acidified to pH 2.0 with concentrated HCl. The CH₂Cl₂ layer was separated and the aqueous layer was extracted with CH₂Cl₂ (3×75 ml). The CH₂Cl₂ solutions were then combined, washed successively with small amounts of brine and water, dried (MgSO₄, anhydrous) and was evaporated to afford title acid as an oil contaminated mainly with impurities derived from n-hexylmesylate. A comparative tlc (silica gel, CH₃OH—CH₂Cl₂, 4:96) examination revealed that the n-hexyl ester or methylester of the title acid were absent in this mixture.

(8) [1R-[1α,2β(Z),3β,4α]]-7-[3-[(Hexyloxy)methyl]-7-oxabicyclo[2.2.1]hept-2-yl]-5-heptenoic acid, methyl ester 1.35 g of the Part (7) acid was dissolved in Et₂O (~30 ml), and a moderate excess of a solution of diazomethane in Et₂O was added. After 5.0 minutes, the excess diazomethane was destroyed by the addition of 2–3 drops of glacial acetic acid. After evaporation of the solvent, the residue was flash-chromatographed on a column of silica gel (LP-1, 40 g) eluting the column with ether-hexane (15:85), with tlc monitoring of the fractions, to isolate slightly impure title methyl ester, (430 mg, 31%) and pure title methyl ester (958 mg, 68%)[1] as oils with consistent IR, H¹-NMR and C¹³-NMR and $[\alpha]_D^{25} + 5.47°$ (C, 2.01; CHCl₃). The total yield was 99%.

Anal. Calcd. for $C_{21}H_{36}O_4$: C, 71.55; H, 10.29. Found: C, 71.29; H, 10.37.

270 MHz H¹-NMR spectrum (CDCl₃): δ 0.9 (t, 3H, J=8.5, CH₃); 1.3 (s, 8 to 9H, CH₂); 2.03 (m, 5H, J=~9.0, CH₂CH=); 2.31 (t, 2H, J=8.5, CH₂ COO) 3.33 (m, 4H, J=9.0, CH₂O); 4.66 (s, 3H, COOCH₃); 4.3 (dd, 2H, J=~5.0 (Δ=59), H₉ and H₁₂); 5.4 (m, 2H, J=~5.0, 14, H₅ and H₆).

1. The H¹-NMR spectrum showed the presence of 3.5 to 4% of the trans-double bond isomer.

B. [1R-[1α,2β(2(R,S),5Z),3β,4α]]-7-[3-[(Hexyloxy)methyl]-7-oxabicyclo[2.2.1]-hept-2-yl]-2-methyl-5-heptenoic acid, methyl ester A solution of diisopropylamine (4.0 mmole, 404 mg) in dry THF (75 ml) was cooled and stirred in a bath at −78° (dry ice-acetone) under nitrogen and 1.7M butyllithium in hexane (3.0 mmole, 1.8 ml) was added. After 5 minutes, a solution of the Part A ester (3.0 mmole, 1.05 g) in dry THF (12 ml) was added dropwise in the course of 5 minutes. After another 15 minutes, methyl iodide (neat, 12 mmole, 1.8 g) was added. After 1.5 hours the solution was allowed to warm to room temperature in the course of about 30 minutes. The mixture was then poured into saturated brine (150 ml) and was extracted with ether (3×80 ml). The extracts were combined, washed with water, dried (MgSO₄ anhydrous) and was evaporated to afford the crude product as an oil (1.0 g). On the basis of tlc, this was a mixture of essentially three compounds: title B compound (major), title A compound (minor) and the polar self-condensation product of the starting ester. In addition, minor impurities more polar than this condensation product were present. This was subjected to a flash chromatography on a silica gel (LPS-1) column to isolate respectively, title compound (650 mg, 59.5%), title A compound (100 mg, 9.5%) and the condensation product (160 mg, 15.8%) with consistent H¹-NMR spectral data.

C. [1R-[1α,2β(5Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (Dry ice-acetone) under an atmosphere of nitrogen and 1.7m n-BuLi in hexane (1.8 mmole, 1.06 ml) was added. After 5 minutes, a solution of Part B compound (1.77 mmole, 650 mg) in dry THF (6.0 ml) was added in the course of 5 minutes. After 10 minutes, methyl iodide (6 mmole, 850 mg) was added. After 1.5 hours, the solution was warmed to room temperature in the course of about 30 minutes. It was then added into 2% hydrochloric acid (75 ml) and was extracted with ether (3×40 ml). The extracts were combined, washed with water (2×20 ml), dried (MgSO$_4$ anhydrous) and was evaporated to afford impure title compound and an oil (640 mg, 95%). This was subjected to a flash chromatography on a silica gel (LPS-1) column to isolate: title compound (400 mg, 59.3%), a mixture of Part B compound and title compound (~1:1, 140 mg, 11%) and Part B compound (80 mg, 12.8%). The title compound was homogeneous (tlc, Et$_2$O-hexane, 1:1) and its H$^1$ and C$^{13}$-NMR spectra were consistent with the structure.

D. [1R-[1α,2β(5Z),3β,4α]]-7-[3-[(Hexyloxy)methyl]-7-oxabicyclo[2.2.1]hept-2-yl]-2,2-dimethyl-5-hepten-1-ol A solution of Part C compound (530 mg, 1.39 mmole) in dry ether (10 ml) was added slowly into a stirred suspension of LiAlH$_4$ (57 mg, 1.5 mmole) in dry ether (25 ml) in an ice bath. The ice bath was then removed and the suspension was stirred at room temperature for 1 hour. It was then recooled in the ice bath and 10% hydrochloric acid was added dropwise until a clear solution resulted. The ether layer was separated and the aqueous layer was extracted once with ether (25 ml). The ether solutions were mixed, washed with a dilute NaHCO$_3$ solution and brine, dried (MgSO$_4$ anhydrous) and was evaporated on a column of silica gel (Baker 60-200 mesh, 20 g), eluting the column with hexane and ether-hexane (1:4) to isolate, after evaporation and drying in vacuo, the analytical specimen of title compound as an oil (460 mg, 93.5%), [α]$_D^{25}$(−)7.24° (c, 4.6; CHCl$_3$) with consistent mass, IR, H$^1$-NMR and C$^{13}$-NMR spectral data.

Anal. Calcd. for C$_{22}$H$_{40}$O$_3$ (MW 352.56): C, 74.95; H, 11.44%. Found: C, 74.64; H, 11.24%.

H$^1$-NMR spectrum (CDCl$_3$, FX-270): δ 0.86 (s, t; 9H, —, H$_{21}$+H$_{22}$+H$_{23}$); 3.30 (m, 6H, —, H$_1$+H$_{14}$+H$_{16}$); 4.16 (d, 1H, J=4.0, H$_9$); 4.36 (d, 1H, J=4.0, H$_{12}$); 5.31 (m, 2H, —, H$_5$+H$_6$);

EXAMPLE 3

[1R-[1α,2β(5Z),3β,4α]]-7-[3-[(Hexyloxy)methyl]-7-oxabicyclo[2.2.1]hept-2-yl]-2,2-dimethyl-5-hepten-1-ol, acetate ester A solution of Example 2 alcohol (300 mg) in dichloromethane (3.0 ml) was mixed with pyridine (1.5 ml) and acetic anhydride (0.75 ml). After 8 hours, the mixture was diluted with ether (75 ml), washed successively with cold 10% hydrochloric acid, dilute NaHCO$_3$ solution and water, dried (MgSO$_4$ anhydrous) and was evaporated to afford the product as an oil. This was chromatographed on a column of silica gel (Baker 60-200 mesh, 15 g), eluting the column successively with hexane and ether-hexane (1:9 and 1:4) to isolate, after drying in vacuo, the analytical specimen of the title compound as a homogeneous (tlc) oil (320 mg, 95%), [α]$_D^{25}$(−) 6.9° (c, 5.0; CHCl$_3$) with consistent mass, IR, H$^1$-NMR and C$^{13}$-NMR spectral data.

Anal. Calcd. for C$_{24}$H$_{42}$O$_4$ (MW 394.60): C, 73.05; H, 10.73%. Found: C, 73.00; H, 10.67%.

H$^1$-NMR Spectrum (CDCl$_3$, FX-270): δ 0.90 (t, 3H, J=~7.0, H$_{21}$); 0.93 (s, 6H, —, H$_{22}$+H$_{23}$); 2.03 (q, 4H, J=~7.0, H$_4$+H$_7$); 2.07 (s, 3H, —, H$_{25}$); 3.35 (m, 4H, —, H$_{14}$+H$_{16}$); 3.79 (s, 0.86H, —, H$_1$); 3.80 (s, 0.14H, —, H$_1$); 4.18 (d, 0.86H, J=~4.0, H$_9$); 4.25 (d, 0.14H, J=~4.0, H$_9$); 4.40 (d, 1H, J=~4.0, H$_{12}$); 5.33 (m, 1H, —, H$_5$+H$_6$).

EXAMPLE 4

[1R-[1α,2β,3β,4α]]-7-[3-[(Hexyloxy)methyl]-7-oxabicyclo[2.2.1]hept-2-yl]-2,2-dimethyl-1-heptanol A solution of [1R-[1α,2β(5Z),3β,4α]]-7-[3-[(hexyloxy)methyl]-7-oxabicyclo[2.2.1]hept-2-yl]-2,2-dimethyl-5-hepten-1-ol (prepared as described in Example 2) (227 mg) in methanol (20 ml) was stirred with 5.0% Pd/C (30 mg) for 18 hours under an atmosphere of hydrogen. The mixture was then filtered through a bed of Celite which was washed with methanol. The filtrate and the washings were combined and was evaporated to afford the title compound. This was subjected to chromatography on a column of silica gel (Baker 60-20 mesh, 15 g), eluting the column with hexane and ether-hexane (1:4 and 3:7) to isolate, after drying in vacuo, the analytical specimen of title compound as an oil (207 mg, 90.8%), [α]$_D^{25}$(−) 3.59° (c, 5.1; CHCl$_3$) with consistent IR, mass H$^1$-NMR and C$^{13}$-NMR spectral data.

Anal. Calcd. for C$_{22}$H$_{42}$O$_3$: C, 74.52; H, 11.94%. Found: C, 74.51; H, 11.84%.

H$^1$-NMR spectrum (CDCl$_3$, FX-270): δ 0.87 (s, 6H, —, H$_{22}$+H$_{23}$); 0.89 (t, 3H, J=~8.0, H$_{22}$); 2.03 (tt, 1H, J=~8.0, unassigned); 3.29 (s, 2H, —, H$_1$); 3.33 (m, 4H, —, H$_{14}$'H$_{16}$); 4.23 (d, 1H, J=~4.0, H$_9$); 4.39 (d, 1H, J=~4.0, H$_{12}$).

EXAMPLE 5

[1R-[1α,2β(2(R,S),5Z),3β,4α]]-7-[3-[(Hexyloxy)methyl]-7-oxabicyclo[2.2.1]hept-2yl]-2-methyl-5-heptenol A suspension of LiAlH$_4$ (2.0 mmole, 76 mg) in dry ether (15.0 ml) was stirred in an ice bath and a solution of [1R-[1α,2β(2RS),5Z,3β,4α]]-7-[3-(hexyloxy)methyl]-7-oxabicyclo[2.2.1]hept-2-yl]-2-methyl-5-heptenoic acid, methyl ester (prepared as described in Example 2, Parts A and B) (1.19 mmole, 435 mg) in dry ether was added in the course of 1 minute. After 5 minutes, the ice bath was removed and the mixture was stirred at room temperature for 1 hour. It was then recooled in the ice bath and 10% hydrochloric acid (10 ml) was added slowly and cautiously (gas evolution). The ether layer was then separated and the aqueous layer was extracted with ether (2×20 ml). The extracts were combined, washed with water, a dilute NaHCO$_3$ solution and water, dried (MgSO$_4$) and was evaporated to afford the analytical specimen of title compound as an oil (390 mg, 97%), [α]$_D^{25}$=(−)4.21° (C, 2.16; CHCl$_3$), with consistent IR, mass $^1$H-NMR and C$^{13}$-NMR spectral data[1].

Anal. Calcd. for C$_{21}$H$_{38}$O$_3$ (MW 338.53): C, 74.51; H, 11.31%. Found: C, 74.34; H, 11.34%.

$^1$H-NMR spectrum (FX-270, CDCl$_3$): δ 0.90 (t, 3H, J=~8.0; H$_{21}$); 0.93, 0.95 (two d, 3H, J=~8.0, H$_{22}$); 3.40 (m, 6H, —, H$_{14}$+H$_{16}$+H$_1$); 4.21 (Singlet, 1H, —, H$_9$); 4.40 (d, 1H, J=~4.0, H$_{12}$); 5.36 (m, 2H, —, H$_5$+H$_6$);

EXAMPLE 6

[1R-[1α,2β(Z),3β,4α]]-7-[3-[(Hexyloxy)methyl]-7-oxabicyclo[2.2.1]hept-2-yl]-5-heptenol A solution of [1R-[1α,2β(Z),3β,4α]]-7-[3-[(hexyloxy)methyl]-7-oxabicyclo[2.2.1]hept-2-yl]-5-heptenoic acid, methyl ester, (prepared as described in Example 2 Part A(8)) (1.0 mmole, 352 mg) in dry ether (5.0 ml) was added into a stirred suspension of LiAlH$_4$ (2.0 mmole, 76 mg) in dry ether (10 ml) in an ice bath. After 6 minutes the ice bath was removed and the suspension was stirred at room temperature for 1 hour. It was then recooled in the ice bath and 10% hydrochloric acid (10 ml) was added dropwise very cautiously (gas evolution). The ether layer was then separated and the water layer was extracted with ether (1×20 ml). The extracts were combined, washed with water, a dilute NaHCO$_3$ solution and water, dried (MgSO$_4$ anhydrous) and was evaporated to afford the analytical specimen of the title compound as a homogeneous (tlc) oil (308 mg, 95%), $[\alpha]_D^{23} = (-) 2.02°$ (C, 2.13; CHCl$_3$), with consistent IR, mass, $^1$H-NMR and C$^{13}$-NMR spectra data.

Anal Calcd for C$_{20}$H$_{36}$O$_3$ (MW 324.51): C, 74.02; H: 11.18%. Found: C, 73.99; H, 11.14%.

$^1$H-NMR spectrum (FX-270, CDCl$_3$): δ 0.89 (t, 3H, J=~8.0, H$_{21}$); 3.35 (m, 4H, J=~8.0, H$_{14}$+H$_{16}$); 3.63 (t, 2H, J=~8.0, H$_1$); 4.20 (d, 1H, J=4.0, H$_9$); 4.40 (d, 1H, J=4.0, H$_{12}$); 5.38 (m, 2H, —, H$_5$+H$_6$).

EXAMPLE 7

[1R-[1α,2β(Z),3β,4α]]-8-[3-[(Hexyloxyl)methyl]-7-oxabicyclo[2.2.1]hept-2-yl]-1-hydroxy-6-octen-2-one A. [1R-[1α,2β(Z),3β,4α]]-7-[3-[(Hexyloxy)methyl]-7-oxabicyclo[2.2.1]hept-2-yl]-5-heptenoyl chloride
and
[1R-[1α,2β(Z),3β,4α]]-8-[3-[(Hexyloxy)methyl]-7-oxabicyclo[2.2.1]hept-2-yl]-1-diazo-6-octen-2-one A solution of [1R-[1α,2β(Z),3β,4α]]-7-[3-[(hexyloxy)methyl]-7-oxabicyclo[2.2.1]hept-2-yl]-5-heptenoic acid (prepared as described in Example 2 (A)(7)) (500 mg, 1.48 mmole) in dry benzene (10 ml) was mixed with oxalyl chloride (0.87 ml, 10 mmole). After 2 hours, the solution was evaporated in vacuo. The residual oil was diluted with dry ether (15 ml) and an approximately three-fold excess of a dry solution of diazomethane in ether was added. Evolution of nitrogen subsided in about 10 minutes. The solution was then concentrated and was dried in vacuo to afford the title diazoketone as an oil (520 mg, 96.8%). A tlc examination (silica gel; Et$_2$-hexane, 3:2) showed the absence of the starting acid, the presence of mainly the diazoketone and a very small amount of a less polar impurity. The IR spectrum showed strong peaks at 2104 (N≡N) and 1645 (c=o) cm$^{-1}$ characteristic of alpha-diazoketones. This material was used in the next step without further characterization.

B. [1R-[1α,2β(Z),3β,4α]]-8-[3-[(Hexyloxy)methyl]-7-oxabicyclo[2.2.1]-hept-2-yl]-1-acetyloxy-6-octen-2-one A solution of the impure Part A diazoketone (520 mg, ~1.43 mmole) in dry dioxane (15 ml) was mixed with glacial acetic acid (1.5 ml) and Cu(OAc)$_2$ (10 mg) and was gradually heated in a bath to 90°-95°. Vigorous evolution of nitrogen started at this temperature and subsided in a few seconds. After another 10 minutes, the mixture was poured into brine (60 ml) and was extracted with ether (3×50 ml). The extracts were combined, washed with water, dried (MgSO$_4$ anhydrous) and was evaporated to afford the crude product as an oil (500 mg). A tlc examination revealed the presence of the minor impurity present in the starting material, mainly the title acetoxyketone and minor amounts of very polar impurities; the starting material was absent. This was purified by a column chromatography on silica gel (25 g; Baker, 60–200 mesh) using Et$_2$O-hexane mixtures for elution to isolate the impurity (30 mg, 5.7%), and the homogeneous (tlc) title acetoxyketone (442 mg, 78.3%). The H$^1$- and C$^{13}$-NMR spectra (CDCl$_3$) of title compound (MW 374.53; C$_{23}$H$_{38}$O$_5$) were consistent with the structural assignment.

C. [1R-[1α,2β(Z),3β,4α]]-8-[3-[(Hexyloxy)methyl]-7-oxabicyclo[2.2.1]hept-2-yl]-1-hydroxy-6-octen-one A solution of Part B acetoxy ketone (246 mg, 0.623 mmole) in methanol (5.0 ml) was stirred with anhydrous K$_2$CO$_3$ (85 mg, 0.623 mmole) under an atmosphere of nitrogen at ambient temperature for 5 minutes. The mixture was then diluted with brine (30 ml) and was extracted with ether (3×20 ml). The extracts were combined, washed with water, dried (MgSO$_4$ anhydrous) and was evaporated in vacuo to afford the homogeneous (tlc) analytical specimen of title compound as an oil (206 mg, 94%), $[\alpha]_D^{25} = +3.95°$ (c, 1.9; CHCl$_3$) with consistent IR, mass, H$^1$- and C$^{13}$-NMR spectral data.

Anal. Calcd. for C$_{21}$H$_{36}$O$_4$ (MW 352.52): C, 71.55; H, 10.30%. Found: C, 71.73; H, 10.18%.

H$^1$-NMR Spectrum (CDCl$_3$; FX-270): δ0.90 (t, 3H, J=~8.0, H$_{21}$); 2.41 (t, 2H, J=~8.0, H$_2$); 3.35 (m, 4H, J=~8.0, H$_{14}$+H$_{16}$); 3.20 (s, 1H, —OH); 4.15 (d, 1H, J=~4.0, H$_9$); 4.40 (d, 1H, J=~4.0, H$_{12}$); 4.21 (d, 2H, J=~4.0, H$_{22}$); 5.38 (m, 2H, —, H$_5$+H$_6$);

EXAMPLE 8

[1R-[1α,2β(5Z),3β,4α]]-7-[3-[(Phenyloxy)methyl]-7-oxabicyclo[2.2.1]hept-2-yl]-2,2-dimethyl-5-hepten-1-ol (a) Phenol (1 mmol) is added to a solution of triphenylphosphine (1 mmol), diethylazodicarboxylate (1 mmol) and title F alcohol from Example 1 (1 mmol) in 25 ml THF and is stirred under an argon atmosphere for 48 hours at 23° C. The reaction mixture is concentrated in vacuo. The residue is triturated with ether and the solids are removed. The filtrate is concentrated in vacuo and chromatographed on silica gel to give [1α,2β(5Z),−3β,4α]-7-[3-[(phenyloxy)methyl]-7-oxabicyclo[2.2.1]hept-2-yl]-5-heptenoic acid, methyl ester.

(b) Following the procedure as set out in Example 2, the ester from part (a) is converted to the title compound.

EXAMPLE 9

[1α,2β(Z),3β,4α]-4-[3-[(Benzyloxy)methyl]-7-oxabicyclo[2.2.1]hept-2-yl]butanol

Following the procedure of Example 1 except substituting benzyl bromide for n-hexyl bromide, the title compound is obtained.

EXAMPLE 10

[1α,2β,3β,4α]-4-[3-[(Cyclohexyloxy)methyl]-7-oxabicyclo[2.2.1]hept-2-yl]butanol

Following the procedure of Example 1 except substituting cyclohexyl bromide for n-hexyl bromide, the title compound is obtained.

EXAMPLE 11

[1R-[1α,2β(5Z),3β,4α]]-7-[3-[(Propoxy)methyl]-7-oxabicyclo[2.2.1]hept-2-yl]-2,2-dimethyl-5-hepten-1-ol Following the procedure of Example 2 except substituting propyl bromide for n-hexyl bromide, the title compound is obtained.

EXAMPLE 12

[1R-[1α,2β(5Z),3β,4α]]-7-[3-[(Ethoxy)methyl]-7-oxabicyclo[2.2.1]hept-2-yl]-2,2-dimethyl-5-hepten-1-ol, acetate ester Following the procedure of Example 3 except substituting methyl bromide for n-hexyl bromide, the title compound is obtained.

EXAMPLE 13

[1R-[1α,2β(5Z),3β,4α]]-7-[3-[(Cycloheptyloxy)methyl]-7-oxabicyclo[2.2.1]hept-2-yl]-2,2-dimethyl-5-hepten-1-ol, acetate ester Following the procedure of Example 3 except substituting cycloheptyl bromide for n-hexyl bromide, the title compound is obtained.

EXAMPLE 14

[1R-[1α,2β(5Z),3β,4α]]-7-[3-[(Benzyloxy)methyl]-7-oxabicyclo[2.2.1]hept-2-yl]-2,2-dimethyl-5-hepten-1-ol acetate ester Following the procedure of Example 3 except substituting benzyl bromide for n-hexyl bromide, the title compound is obtained.

EXAMPLE 15

[1R-[1α,2β,3β,4α]]-7-[3-[(Cyclopentylmethyloxy)methyl]-7-oxabicyclo[2.2.1]hept-2-yl]-2,2-dimethyl-1-heptanol Following the procedure of Example 4 except substituting cyclopentylmethyl bromide for n-hexyl bromide, the title compound is obtained.

EXAMPLE 16

[1R-[1α,2β(Z,R,S),3β,4α]]-7-[3-[(Cyclohexyloxy)methyl]-7-oxabicyclo[2.2.1]hept-2-yl]-2-methyl-5-heptenol Following the procedure of Example 5 except substituting cyclohexyl bromide for n-hexyl bromide, the title compound is obtained.

EXAMPLE 17

[1R-[1β,2α(Z),3α,4β]]-7-[3-[(Propoxy)methyl]-7-oxabicyclo[2.2.1]hept-2-yl]-2-methyl-5-heptenol Following the procedure of Example 5 except substituting propyl bromide for n-hexyl bromide, the title compound is obtained.

EXAMPLE 18

[1R-[1α,2β(Z),3β,4α]-7-[3-[(Methoxy)methyl]-7-oxabicyclo[2.2.1]hept-2-yl]-5-heptenol Following the procedure of Example 6 except substituting methyl bromide for n-hexyl bromide, the title compound is obtained.

EXAMPLE 19

[1R-[1α,2β(Z),3β,4α]]-7-[3-[(Cyclohexyloxy)methyl]-7-oxobicyclo[2.2.1]hept-2-yl]-5-heptenol Following the procedure of Example 6 except substituting cyclohexyl bromide for n-hexyl bromide, the title compound is obtained.

EXAMPLE 20

[1R-[1α,2β(Z),3β,4α]]-7-[3-[(Benzyloxy)methyl]-7-oxabicyclo[2.2.1]hept-2-yl]-5-heptenol Following the procedure of Example 6 except substituting benzyl bromide for n-hexyl bromide, the title compound is obtained.

EXAMPLE 21

[1R-[1α,2β(5Z),3β,4α]]-7-[3-[(Cyclohexylmethyloxy)methyl]-7-oxabicyclo[2.2.1]hept-2-yl]-]-5-heptenol Following the procedure of Example 6 except substituting cyclohexylmethyl bromide for n-hexyl bromide, the title compound is obtained.

EXAMPLE 22

[1R-[1α,2β(Z),3β,4α]]-7-[3-[(Phenyloxy)methyl]-7-oxabicyclo[2.2.1]hept-2-yl]-5-heptenol Following the procedure of Examples 6 and 8 except substituting the Example 8 Part (a) ester for the Example 2 Part A(8) ester, the title compound is obtained.

EXAMPLE 23

[1R-[1α,2β(Z),3β,4α]]-8-[3-[(Benzyloxy)methyl]-7-oxabicyclo[2.2.1]hept-2-yl]-1-hydroxy-6-octen-2-one Following the procedure of Examples 2 and 7 except substituting benzyl bromide for hexyl bromide, the title compound is obtained.

EXAMPLE 24

[1R-[1α,2β(Z),3β,4α]]-8-[3-[(Cyclopropyloxy)methyl]-7-oxabicyclo[2.2.1]hept-2-yl]-1-hydroxy-6-octen-2-one Following the procedure of Examples 2 and 7 except substituting cyclopropyl bromide for hexyl bromide, the title compound is obtained.

EXAMPLE 25

[1R-[1α,2β(Z),3β,4α]]-8-[3-[(Cyclohexylethyloxy)methyl]-7-oxabicyclo[2.2.1]hept-2-yl]-1-hydroxy-6-octen-2-one Following the procedure of Examples 2 and 7 except substituting cyclohexylethyl bromide for hexyl bromide, the title compound is obtained.

EXAMPLE 26

[1R-[1α,2β(Z),3β,4α]]-8-[3-[(Butyloxy)methyl]-7-oxabicyclo[2.2.1]hept-2-yl]-1-hydroxy-6-octen-2-one Following the procedure of Examples 2 and 7 except substituting butyl bromide for hexyl bromide, the title compound is obtained.

EXAMPLE 27

[1R-[1α,2β(5Z),3β,4α]]-7-[3-[(Phenyloxy)methyl]-7-oxabicyclo[2.2.1]hept-2-yl]-2,2-dimethyl-5-hepten-1-ol, benzoic acid ester Following the procedure of Examples 3 and 8 except substituting benzoyl chloride for acetic anhydride, the title compound is obtained.

EXAMPLE 28

(1α,2β,3β,4α)-7-[3-[(Benzyloxy)methyl]-7-oxabicyclo[2.2.1]hept-2-yl]-2,2-dimethyl-5-hepten-1-ol, Following the procedure of Examples 2 and 5 except substituting benzyl bromide for hexyl bromide, the title compound is obtained.

EXAMPLE 29

[1R-[1α,2β(5Z),3β,4α]]-7-[3-[2-(Hexyloxy)ethyl]-7-oxabicyclo[2.2.1]hept-2-yl]-2,2-dimethyl-5-hepten-1-ol A. [1α,2β(Z),3β,4α]-7-[3-(2-Oxo)ethyl]-7-oxabicyclo[2.2.1]hept-2-yl]-5-heptenoic acid, methyl ester Into a dry 100 ml round bottom 3-necked flask containing a stir bar was added dried 12.9 g (37.7 mmoles) methoxymethyltriphenylphosphonium chloride ((C$_6$H$_5$)$_3$P$^+$—CH$_2$OCH$_3$Cl$^-$) and 235 ml distilled toluene (stored over molecular sieves). The resulting suspension was stirred in an ice-bath, under argon, until cold and a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1α,2β(Z),3β,4α]-7-[3-formyl-7-oxabicyclo[2.2.1]hept-2-yl]-5-heptenoic acid, methyl ester in 60 ml toluene was added by means of a dropping funnel over a 35 minute period with the ice-bath still in place. The reaction was then quenched by addition of 2.3 g (39 mmol) acetic acid in 5 ml ether. The reaction mixture immediately turned pale yellow and was immediately poured into 200 ml saturated NH$_4$Cl, and extracted with ether (4×200 ml). The combined ether phases were washed with NaCl saturated solution, and dried (MgSO$_4$) and concentrated to yield a yellow oil in a white crystalline solid (phosphine oxide). The white solid was triturated with EtOAc and the mother liquor was purified by chromatography on an LPS-1 silica column. The fractions obtained were (A) [1α,2β(Z),3β,4α]-7-[3-(2-oxo)ethyl-7-oxabicyclo[2.2.1-]hept-2-yl]-5-heptenoic acid, methyl ester, (B) [1α,2β(Z),3β,4α]-7-[3-(2-methoxy)ethendiyl]-7-oxabicyclo[2.2.1]hept-2-yl]-5-heptenoic acid, methyl ester and (C) [1α,2β(Z),3β,4α]-7-[3-(2,2-dimethoxy)ethyl-7-oxabicyclo[2.2.1]hept-2-yl]-5-heptenoic acid, methyl ester.

Compounds (B) and (C) are each treated with aqueous trifluoroacetic acid to convert each to compound (A).

B. [1α,2β(Z),3β,4α]-7-[3-(2-Hydroxyethyl)-7-oxabicyclo[2.2.1]hept-2-yl]-5-heptenoic acid, methyl ester The aldehyde (1.4 g, 5 mmol) from part A in methanol (50 ml) was treated with NaBH$_4$ (0.19 g, 5 mmol) in an argon atmosphere at 0° C. After stirring at 0° C. for 1 hour, the reaction was quenched by addition of 2N HCl (to pH 2). The methanol was removed in vacuo and the reaction mixture was taken up in ether. The ether solution was washed with saturated KHCO$_3$, saturated NaCl and dried (MgSO$_4$). The ether was evaporated to yield the title B compound.

C. [1R-[1α,2β(5Z),3β,4α]]-7-[3-[2-(Hexyloxy)ethyl]-7-oxabicyclo[2.2.1]-hept-2-yl]-2,2-dimethyl-5-hepten-1-ol Following the procedure of Example 2 except substituting the above part B alcohol for the alcohol used in Example 2, Part (7), the title compound is obtained.

EXAMPLE 30

[1R-[1β,2α,3α,4β]]-7-[3-[2-(Hexyloxy)ethyl]-7-oxabicyclo[2.2.1]hept-2-yl]-2,2-dimethyl-1-heptanol Following the procedure of Examples 2 and 4, except substituting (1α,2β,3β,4α)-7-[3-(hydroxymethyl)-7-oxabicyclo[2.2.1]hept-2-yl]heptanoic acid, methyl ester for [1α,2β(Z),3β,4α]-7-[3-(hydroxymethyl)-7-oxabicyclo[2.2.1]hept-2-yl]-5-heptenoic acid, methyl ester, the title compound is obtained.

EXAMPLE 31

[1R-[1α,2β(Z),3β,4α]]-7-[3-[2-(Benzyloxy)ethyl]-7-oxabicyclo[2.2.1]hept-2-yl]-2,2-dimethyl-5-hepten-1-ol Following the procedure of Examples 2 and 29 except substituting benzyl bromide for n-hexyl bromide, the title compound is obtained.

EXAMPLE 32

[1R-[1α,2β(Z),3β,4α]]-7-[3-[2-(Cyclohexyloxy)ethyl]-7-oxabicyclo[2.2.1]hept-2-yl]-2,2-dimethyl-5-hepten-1-ol Following the procedure of Examples 2 and 29 substituting cyclohexyl bromide for hexyl bromide, the title compound is obtained.

EXAMPLE 33

[1R-[1α,2β(Z),3β,4α]]-7-[3-[4-(Hexyloxy)butyl]-7-oxabicyclo[2.2.1]hept-2-yl]-2,2-dimethyl-5-hepten-1-ol A. [1α,2β(5Z),3β,4α]-7-[3-(3-Oxo)propyl-7-oxabicyclo[2.2.1]hept-2-yl]-5-heptenoic acid, methyl ester Following the procedure of Example 29, part A except substituting [1α,2β(Z),3β,4α]-7-[3-(2-oxo)-ethyl-7-oxabicyclo[2.2.1]hept-2-yl]-5-heptenoic acid, methyl ester for [1α,2β(Z),3β,4α]-7-[3-formyl-7-oxabicyclo[2.2.1]hept-2-yl]-5-heptenoic acid, methyl ester, the title A compound is obtained.

B. [1α,2β(Z),3β,4α]-7-[3-(4-Oxo)butyl-7-oxabicyclo[2.2.1]hept-2-ylα-5-heptenoic acid, methyl ester Following the procedure of Example 29, part A, except substituting the aldehyde from part A above, for [1α,2β(Z),3β,4α]-7-[3-(2oxo)ethyl-7-oxabicyclo[2.2.1-]hept-2-yl]-5-heptenoic acid, methyl ester, the title B aldehyde is obtained.

C. [1R-[1α,2β(Z),3β,4α]]-7-[3-[4-(Hexyloxy)butyl]-7-oxabicyclo[2.2.1]hept-2-yl]-2,2-dimethyl-5-hepten-1-ol Following the procedure of Example 29, part B, except substituting the title B aldehyde for [1α,2β(Z),3β,-4α]-7-[3-(2-oxo)ethyl-7-oxabicyclo[2.2.1]hept-2-yl]-5-heptenoic acid, methyl ester, the title C alcohol is obtained.

EXAMPLE 34

[1R-[1α,2β,3β,4α]]-7-[3-[4-(Cyclohexyloxy)butyl]-7-oxabicyclo[2.2.1]hept-2-yl]-2,2-dimethyl-1-heptanol Following the procedure of Examples 29, 33 and 4 except substituting cyclohexyl bromide for n-hexyl bromide, the title compound is obtained.

EXAMPLE 35

[1R-[1α,2β(Z),3β,4α]]-7-[3-[4-(Benzyloxy)butyl]-7-oxabicyclo[2.2.1]hept-2-yl]-2,2-dimethyl-5-hepten-1-ol Following the procedure of Examples 2, 29, 33 and 34 except substituting benzyl bromide for n-hexyl bromide, the title compound is obtained.

EXAMPLE 36

[1R-[1α,2β(5Z),3β,4α]]-7-[3-[(Hexyloxy)methyl]-7-oxabicyclo[2.2.1]hept-2-yl]-2,2-dimethyl-5-heptene-1-ol, L-phenylalanyl ester A. [1R-[1α,2β(5Z),3β,4α]]-7-[3-[(Hexyloxy)methyl]-7-oxabicyclo[2.2.1]hept-2-yl]-2,2-dimethyl-5-heptene-1-ol, N-t-butoxy carboxyl-L-phenylalanyl ester A solution of N-t-BOC-L-phenylalanine (451 mg; 1.7 mmole), dicyclohexyldicarbodiimide (350.8 mg; 1.7 mmole) and 4-dimethylaminopyridine (209.8 mg, 1.7 mmole) in dry distilled tetrahydrofuran (15 ml) was stirred at 0° under $N_2$ for 1 hour. A solution of the alcohol product of Example 2 (300 mg; 0.851 mmole) in dry tetrahydrofuran (10 ml) was then added dropwise and the reaction mixture stirred at 0° under $N_2$ for 2 hours. The precipitates that formed were filtered off and the clear filtrate was evaporated to dryness. The semi-solid obtained was dissolved in dichloromethane (100 ml), washed successively with 1N HCl (20 ml), $H_2O$ (20 ml), 5% $NaHCO_3$ (20 ml) and $H_2O$ (20 ml), dried (anhyd. $MgSO_4$) and evaporated to dryness.

The above product mixture was chromatographed (flash) on a silica gel column (LPS-1), eluting the column with $Et_2O$:hexane (1:9, 1.5 liters) and $Et_2O$:hexane (1:4, 2.0 liters). The desired fractions (TLC) were combined and evaporated to dryness to give an oil (388 mg, 76%) with an $H^1$ NMR-spectrum consistent for the pure 5,6-Cis double bond isomer. [An additional amount (134 mg) eluted later was a 1:1 mixture of the 5,6-cis and 5,6-trans isomers. The yield was therefore quantitative.]

B. [1R-[1α,2β(5Z),3β,4α]]-7-[3-[(Hexyloxy)methyl]-7-oxabicyclo[2.2.1]hept-2-yl]-2,2-dimethyl-5-heptene-1-ol, L-phenyl alanyl ester A solution of Part A compound (330 mg; 0.55 mmole) was dissolved in dry dichloromethane (12 ml), cooled down to 0° under $N_2$, treated with trifluoroacetic acid (2.4 ml) and stirred overnight at 0°. The reaction mixture was evaporated to dryness and the oil obtained dissolved in ethyl acetate (120 ml), washed with 5% $NaHCO_3$ (30 ml) and $H_2O$ (30 ml), dried (anhydrous $MgSO_4$) and evaporated to dryness. The crude product was combined with that obtained from a previous run (0.096 mmole) and the entire amount (302 mg) was chromatographed (gravity) on a silica gel column (Baker; 100 ml), eluting the column with $CH_2Cl_2$ (50 ml) and $CH_2Cl_2$:$CH_3OH$ (98:2; 500 ml). The desired fractions were combined, evaporated and dried in vacuo to give an analytical specimen of the title compound (297.4 mg; 92.2%) as a homogeneous oil (TLC) with consistent IR (1733 cm$^{-1}$, strong, c=o), mass, $H^1$- and $C^{13}$-spectral data.

Anal. Calcd. for $C_{31}H_{49}NO_4$: C, 74.51; H, 9.88; N, 2.80%. Found: C, 74.56; H, 9.91; N, 2.67%.

$H^1$-NMR Spectrum (CDCl$_3$, FX-270) δ0.91 (t, 9H, —, $H_{21}$, $H_{22}$+$H_{23}$); 1.22–2.1 (m, 21H, —, —); 2.88 (q, 1H, J=~8.0, $H_{26}$); 3.08 (q, 1H, J=~8.0, $H_{26}$); 3.26–3.42 (m, 4H, —, $H_{14}$+$H_{16}$); 3.80 (m, 1H, J=~7.0, $H_{25}$); 3.83 (d, 2H, J=~4.0, $H_1$); 4.18 (d, 1H, J=~4, $H_9$); 4.40 (d, 1H, J=~4, $H_{12}$); 5.33 (m, 2H, —, $H_5$+$H_6$); 7.16–7.36 (m, 5H, —, aromatic protons).

EXAMPLE 37

[1R-[1α,2β(5Z),3β,4α]]-7-[3-[(Propyloxy)methyl]-7-oxabicyclo[2.2.1]hept-2-yl]-2,2-dimethyl-5-heptenol, glycine ester Following the procedure of Examples 2 and 36 except substituting propyl mesylate for n-hexyl mesylate and t-Boc-glycine for Na-t-BOC-L-phenylalanine, the title compound is obtained.

EXAMPLE 38

[1R-[1α,2β(5Z),3β,4α]]-7-[3-[(Cyclohexyloxy)methyl]-7-oxabicyclo[2.2.1]hept-2-yl]-2,2-dimethyl-5-heptenol, alanine ester Following the procedure of Examples 2 and 36 except substituting cyclohexyl mesylate for n-hexyl mesylate and t-Boc-alanine for Na-t-BOC-L-phenylalanine, the title compound is obtained.

EXAMPLE 39

[1R-[1α,2β(5Z),3β,4α]]-7-[3-[(Benzyloxy)methyl]-7-oxabicyclo[2.2.1]hept-2-yl]-2,2-dimethyl-5-heptenol, histidine ester Following the procedure of Examples 2 and 36 except substituting benzyl mesylate for n-hexyl mesylate and bis-t-Boc histidine for Na-t-BOC-L-phenylalanine, the title compound is obtained.

EXAMPLE 40

[1R-[1α,2β,3β,4α]]-7-[3-[(Hexyloxy)methyl]-7-oxabicyclo[2.2.1]hept-2-yl]-2,2-dimethyl-1-heptanol, proline ester Following the procedure of Examples 2 and 36 except substituting t-Boc-proline for Na-t-BOC-L-phenylalanine, the title compound is obtained.

EXAMPLE 41

[1R-[1α,2β,3β,4α]]-7-[3-[(Butyloxy)methyl]-7-oxabicyclo[2.2.1]hept-2-yl]-2,2-dimethyl-1-heptanol, lysine ester Following the procedure of Example 36 except substituting butyl mesylate for n-hexyl mesylate and bis-t-Boc-lysine for Na-t-BOC-L-phenylalanine, the title compound is obtained.

EXAMPLE 42

[1R-[1α,2β,3β,4α]]-7-[3-[(Cyclopentyloxy)methyl]-7-oxabicyclo[2.2.1]hept-2-yl]-2,2-dimethyl-1-heptanol, leucine ester Following the procedure of Example 36 except substituting cyclopentyl mesylate for n-hexyl mesylate and t-Boc-leucine for Na-t-BOC-L-phenylalanine, the title compound is obtained.

EXAMPLE 43

[1R-[1α,2β(Z),3β,4α]]-7-[3-[(Hexyloxy)methyl]-7-oxabicyclo[2.2.1]hept-2-yl]-2,2-dimethyl-5-heptenoic acid, 1-(1-oxopropoxy)propyl ester A. [3aR-[1-(1R,2S,5R),3aα,4α,7α,7aα]]-Octahydro-1-[[5-methyl-2-(1-methylethyl)cyclohexyl]oxy]-4,7-epoxyisobenzofuran A solution of (exo)-octahydro-4,7-epoxyisobenzofuran-1-ol prepared as described in U.S. Pat. No. 4,143,054 (21 g, 0.13 mole), levo-menthol (21 g, 0.18 mole) and p-toluene-sulfonic acid (trace) in benzene (500 ml) was heated at reflux for 24 hours under nitrogen with a Dean-Stark trap containing molecular sieves in the system. The solution was chilled, washed with 5% sodium bicarbonate (200 ml), then concentrated in vacuo. The residue was recrystallized from methanol (300 ml) to yield 10 g of [3aR-[1-(1R,2S,5R),3aα,4α,7α,-

7aα]]-octahydro-1-[[5-methyl-2-(1-methylethyl)cyclohexyl]oxy]-4,7-epoxyisobenzofuran, m.p. 109°–111° C.

B. [3aS-(3aα,4α,7α,7aα)]-Octahydro-1-benzyloxy-4,7-epoxyisobenzofuran

A solution of [3aR-[1-(1R,2S,5R),3aα,4α,7α,7aα]]-octahydro-1-[[5-methyl-2-(1-methylethyl)cyclohexyl]oxy]-4,7-epoxy-isobenzofuran (from Part A) (11.8 g, 0.04 mole) and p-toluenesulfonic acid (trace) in benzyl alcohol (120 ml) was heated at 120° C. under nitrogen for 4 hours. After this time, TLC (silica gel; ether/hexane (1:1)) indicated complete absence of starting material. The mixture was chilled, dissolved in ether, washed with 5% sodium bicarbonate and brine, dried over magnesium sulfate and concentrated in vacuo. Excess benzyl alcohol was removed by distillation. The residue was purified by flash chromatography on LP-1 silica gel (700 ml) eluting with 20% and 50% ether/hexane mixtures to yield 750 mg of title compound as an oil.

TLC: silica gel; hexane/ether (1:1), $R_f=0.25$; vanillin spray and heat.

C. [3aS-(3aα,4α,7α,7aα)]-Octahydro-4,7-epoxyisobenzofuran-1-ol

A mixture of title B compound (7.8 g, 0.032 mole), and 10% Pd/C (1 g) in ethyl acetate (250 ml) was stirred under one atmosphere of hydrogen until 707 ml of hydrogen had been consumed. The mixture was filtered and concentrated in vacuo. The residue was purified by flash chromatography with LP-1 silica gel (500 ml) eluting with ethyl acetate/dichloromethane (1:4) to yield 3.8 g of optically active title compound, m.p. 125° C.

$[\alpha]_D = -44°$, $[\alpha]^{Hg}_{365} = -122°$ (c=10 mg/ml, MeOH).

TLC: silica gel; ethyl acetate/dichloromethane (1:1), $R_f=0.2$; vanillin spray and heat.

D. [1R-(1α,2β,3β,4α)]-3-(Hydroxymethyl)-2-(2-methoxyethenyl)-7-oxabicyclo-[2.2.1]heptane A slurry of methoxymethyltriphenylphosphonium chloride (28.1 g, 0.082 mole) in toluene (700 ml) was treated with a solution of lithium diisopropylamide [prepared from 1.6M n-butyl lithium (51 ml, 0.082 mole) and diisopropylamine (14.25 ml, 0.10 mole) in pentane] in tetrahydrofuran (20 ml). The mixture was stirred at room temperature for 30 minutes then treated with title C compound (3.7 g, 0.024 mole) dissolved in toluene (20 ml). The mixture was stirred at room temperature for 2 days. The reaction mixture was then poured into brine, acidified to pH=5 with concentrated hydrochloric acid, and extracted with ether (3×500 ml). The combined ether extracts were dried over anhydrous magnesium sulfate and concentrated in vacuo. The residue was triturated with hexane/ether and filtered. The filtrate was concentrated in vacuo and the residue chromatographed on LP-1 silica gel (300 ml) eluting with pentane/ether (1:1) and ether to yield the desired title B product contaminated with phosphine oxide. This product was distilled in vacuo to yield 3 g of title D compound, b.p. 90° C./0.01 mm.

$[\alpha]_D = +44°$, $[\alpha]^{Hg}_{365} = +138°$ (c=11 mg/ml, MeOH).

TLC: silica gel; ethyl acetate/dichloromethane (1:1); $R_f=0.2$; vanillin spray and heat.

E. [4aS-(4aα,5α,8α,8aα)]-Octahydro-5,8-epoxy-(1H)-benzopyran-3-ol

A solution of title D compound (3 g, 0.016 mole) in 20% trifluoroacetic acid/water (30 ml) was stirred at room temperature under nitrogen for 2 hours. The solution was made basic with solid sodium bicarbonate. The aqueous solution was then saturated with sodium chloride and extracted with dichloromethane (6×200 ml). The combined extracts were concentrated in vacuo. The resultant oil contained significant amounts of partial hydrolysis products. This material was subjected to a second treatment with TFA as above and after a second workup as before yielded a solid which was recrystallized from cyclohexane to yield 2.4 g of title E compound, m.p. 104°–105° C.

$[\alpha]_D = +27.2°$, $[\alpha]^{Hg}_{365=0°}$ (c=7.9 mg/ml, MeOH).

F. [1R-[1α,2β(5Z),3β,4α]]-7-[3-(Hydroxymethyl)-7-oxabicyclo[2.2.1]hept-2-yl]-5-heptenoic acid, methyl ester A slurry of 4-carboxybutyltriphenylphosphonium bromide (18.8 g, 0.0434 mole) in anhydrous dimethyl sulfoxide (36 ml) was treated with a solution of freshly prepared dimsyl ion at 15° C. until an orange coloration persisted. A second equivalent of dimsyl ion was added to form the desired ylide. The deep red mixture was stirred at room temperature for 30 minutes, then treated with title E compound (2.4 g, 0.0141 mole). The reaction mixture was stirred at room temperature for 2 hours then quenched with a solution of glacial acetic acid (2.58 g) in ether (10 ml). The mixture was poured into brine (1000 ml), acidified to pH=2 with concentrated hydrochloric acid and extracted with ethyl acetate (5×300 ml). The combined extracts were concentrated in vacuo. The residue was dissolved in 5% sodium bicarbonate and extracted with benzene (2×100 ml) and ethyl acetate (2×100 ml). The aqueous solution was then acidified to pH=2 with concentrated hydrochloric acid and extracted with ether (7×200 ml). The combined ether extracts were dried over magnesium sulfate and concentrated in vacuo. The residue was dissolved in ether (300 ml) and chilled overnight. The precipitated phosphine salts were removed by filtration. The filtrate was treated with excess diazomethane solution and stirred at room temperature for 1 hour. The reaction mixture was quenched with glacial acetic acid, washed with 5% sodium bicarbonate, then concentrated in vacuo. The residue was purified by flash chromatography on LP-1 silica gel (600 ml) eluting with hexane/ether (1:1) and ether to yield 3 g of title compound.

$[\alpha]_D = +11.2°$, $[\alpha]^{Hg}_{365=0°}$ (c=16.9 mg/ml, MeOH).

TLC: silica gel; ether; $R_f=0.4$; vanillin spray and heat.

G. [1R-[1α,2β(Z),3β,4α]]-7-[3-[(Hexyloxy)methyl]-7-oxabicyclo[2.2.1]hept-2-yl]-5-heptenoic acid, hexyl ester A mixture of powdered KOH (0.93 g) in 25 ml of dry xylene was heated to reflux under argon atmosphere and 12 ml of xylene was removed by distillation. To this mixture was added a solution of 500 mg (1.86 mmol) of title F alcohol methyl ester in 16 ml of dry xylene. The volume of the reaction mixture was reduced 12 ml by distillative removal of xylene. To the reaction mixture was then added a solution of 1.68 g (9.30 mmol) hexylmesylate in 16 ml of dry xylene. This mixture was refluxed for 1 hour and 15 minutes. The cooled reaction mixture was diluted with 100 ml of saturated NaHCO$_3$ solution and extracted with CH$_2$Cl$_2$ (3×100 ml). The combined CH$_2$Cl$_2$ extracts were washed with brine (1×200 ml), dried (MgSO$_4$), filtered and concentrated in vacuo. Purification was effected by flash chromatography on 46 g of silica gel 60 using hexane:ethane (5:1) as eluant. This gave 0.62 g of title hexyl ester (79%) as a colorless oil. TLC: silica gel, 2% CH$_3$OH/CH$_2$Cl$_2$, $R_f$ 0.80, iodine.

H.  1R-[1α,2β(Z),3β,4α]]-7-[3-[(Hexyloxy)methyl]-7-oxabicyclo[2.2.1]hept-2-yl]-5-heptenoic acid To a stirred solution of 517 mg (1.12 mmol) of Part G hexyl ester, 55 ml of distilled THF, 4.40 ml of CH₃OH and 7.20 ml of H₂O under argon was added 13.50 ml of 1N aqueous lithium hydroxide solution. This mixture was purged with argon vigorously for 30 minutes and stirred at room temperature for 15 hours. The reaction mixture was acidified to pH 3 by the addition of 1N aqueous HCl solution. The resulting solution was poured into 120 ml of saturated NaCl solution and was saturated with solid NaCl. The aqueous layer was extracted with EtOAc (4×150 ml). The combined EtOAc extracts were dried (MgSO₄), filtered and concentrated in vacuo. This was chromatographed on 40 g of silica gel 60 using 4% $CH_3OH$ in $CH_2Cl_2$ as eluant to give the desired product contaminated with a small amount of hexyl alcohol. The product was pumped under high vacuum for ~60 hours at room temperature to give 350 mg (85%) of pure title acid. TLC: silica gel, 4% $CH_3OH/CH_2Cl_2$, $R_f$=0.42, iodine.

$[\alpha]_D$= +5.2° (CHCl₃).

Anal. Calcd. for $C_{20}H_{34}O_4$: C, 70.92; H, 10.12%. Found: C, 70.66; H, 9.99%.

I.  [1R-[1α,2β(Z),3β,4α]]-7-[3-[(Hexyloxy)methyl]-7-oxabicyclo[2.2.1]hept-2-yl]-5-heptenoic acid, methyl ester

[1R-[1α,2β(Z),3β,4α]]-7-[3-[(Hexyloxy)methyl]-7-oxabicyclo[2.2.1]hept-2-yl]-5-heptenoic acid (1.35 g, 4 mmole, prepared as described in Part H) was dissolved in Et₂O (~30 ml) and a moderate excess of a solution of diazomethane in Et₂O was added. After 5 minutes, the excess diazomethane was destroyed by the addition of 2-3 drops of glacial acetic acid. After evaporation of the solvent the residue was flash-chromtographed on a column of silica gel (LP-1, 40 g) eluting the column with ether-hexane (15:85), with tlc monitoring of the fractions, to isolate slightly impure title ester (430 mg, 31%) and pure title ester (958 mg, 68%)[1] as oils with consistent IR, mass H¹-NMR and C¹³-NMR spectra and $[\alpha]_D^{25}$ +5.47° (C, 2.01; CHCl₃).

Anal. Calcd. for $C_{21}H_{36}O_4$: C, 71.55; H, 10.29%. Found: C, 71.29; H, 10.37%.

270 MHz H¹-NMR spectrum (CDCl₃): δ 0.9 (t, 3H, J=8.5, CH₃); 1.3 (s, 8 to 9H, CH₂); 2.03 (m, 5H, J=~9.0, CH₂CH=); 2.31 (t, 2H, J=8.5, CH₂COO); 3.33 (m, 4H, J=9.0, CH₂O); 4.66 (s, 3H, COOCH₃); 4.15 (d, 1H, J=~5.0, H₉); 4.38 (d, 1H, J=~5.0, H₁₂); 5.4 (m, 2H, J=~5.0, 14, H₅ and H₆).

J.  [1R-[1α,2β(2(R,S),5Z),3β,4α]]-7-[3-[(Hexyloxy)methyl]-7-oxabicyclo[2.2.1]-hept-2-yl]-b 2-methyl-5-heptenoic acid, methyl ester A solution of diisopropylamine (4.0 mmole, 404 mg) in dry THF (75 ml) was cooled and stirred in a bath at −78° (Dry ice-acetone) under nitrogen and 1.7M butyllithium in hexane (3.0 mmole, 1.8 ml) was added. After 5 minutes, a solution of the Part I ester (3.0 mmole, 1.05 g) in dry THF (12 ml) was added dropwise in the course of 5 minutes. After another 15 minutes, hexamethylphosphoric amide (0.5 ml) and methyl iodide (neat, 12 mmole, 1.8 g) were added. After 1.5 hours, the solution was allowed to warm to room temperature in the course of about 30 minutes. The mixture was then poured into saturated brine (150 ml) and was extracted with ether (3×80 ml). The extracts were combined, washed with water, dried (MgSO₄ anhydrous) and evaporated to afford the crude product as an oil (1.0 g). On the basis of tlc, this was a mixture of essentially two compounds: title ester (major), and Example 60 ester (minor). In addition, minor, more polar impurities were present. This was subjected to a flash chromatography on a silica gel (LPS-1) column to isolate respectively, title ester (650 mg, 59.5%), and Part I ester (100 mg, 9.5%).

K.  [1R-[1α,2β(Z),3β,4α]]-7-[3-[(Hexyloxy)methyl]-7-oxabicyclo[2.2.1]hept-2-yl]-2,2-dimethyl-5-heptenoic acid, methyl ester A solution of dry isopropylamine (2.0 mmole, 202 mg) in dry THF (12 ml) was cooled and stirred in a bath at −78° (Dry ice-acetone) under an atmosphere of nitrogen and 1.7M n-BuLi in hexane (1.8 mmole, 1.06 ml) was added. After 5.0 minutes, a solution of [1R-[1α,2β(2(R,S),5Z),3β,4α]]-7-[3-[(hexyloxy)methyl]-7-oxabicyclo[2.2.1]hept-2-yl]-2-methyl-5-heptenoic acid, methyl ester prepared as described in Part J (1.77 mmole, 650 mg) in dry THF (6.0 ml) was added in the course of 5 minutes. After 10 minutes, methyl iodide (6.0 mmole, 850 mg) was added. After 1.5 hours, the solution was warmed to room temperature in the course of about 30 minutes. It was then added into 2% hydrochloric acid (75 ml) and was extracted with ether (3×40 ml). The extracts were combined, washed with water (2×20 ml), dried (MgSO₄ anhydrous) and evaporated to afford impure title methyl ester and an oil (640 mg, 95%). This was subjected to a flash chromatography on a silica gel (LPS-1) column to yield: title ester (400 mg, 59.3%), a mixture of Part J ester and title ester (~1:1, 140 mg, 11%) and Part J ester (80 mg, 12.8%). The title ester was homogeneous (tlc, Et₂O-hexane, 1:1) and its H¹ and C¹³-NMR spectra were consistent with the structure.

L.  [1R-[1α,2β(Z),3β,4α]]-7-[3-[(Hexyloxy)methyl]-7-oxabicyclo[2.2.1]hept-2-yl]-2,2-dimethyl-5-heptenoic acid A solution of Part K ester (233 mg, 0.612 mmole) in THF (4.0 ml) was mixed with 1N LiOH (4.0 ml) and was stirred under an atmosphere of nitrogen for 24 hours. No hydrolysis was observed by tlc of an acidified (dil. HCl) aliquot. Therefore, solid LiOH·1H₂O (12 mmole, 504 mg) was added and the mixture was stirred under reflux for 48 hours resulting in complete hydrolysis. The mixture was then cooled to ambient temperature, acidified with concentrated HCl (to pH 2.5) diluted with brine (20 ml) and was extracted with ether (3×20 ml). The extracts were combined, washed with water (2×100 ml), dried (MgSO₄ anhydrous) and evaporated to afford the crude product as an oil (210 mg). This was subjected to a column chromatography on silica gel (Baker, 60–200 mesh, 10 g), eluting the column with hexane and Et₂O-hexane mixtures (15:85, 1:3) to isolate homogeneous (tlc) title acid as an oil (200 mg, 89%), $[\alpha]_D^{23}$=(+) 1.16° (c, 2.2; CHCl₃), with consistent IR, mass, H¹− and C¹³-NMR spectral data.

Anal. Calcd. for C₂₂H₃₈O₄ (MW 366.54): C, 72.08; H, 10.46%. Found: C, 72.16; H, 10.37%.

H¹-NMR Spectrum (FX-270, CDCl₃): δ 0.90 (t, 3H, J=~8.0, H₂₁); 1.23 (s, 6H, —, H₂₂+H₂₃); 2.03 (m, 4H, J=~8.0, H₄+H₇); 3.35 (m, 4H, J=~8.0, H₁₄+H₁₆); 4.2 (d, 1H, J=~4.0, H₉); 4.43 (d, 1H, J=~4.0, H₁₂); 5.35 (m, 1H, —, H₅+H₆);

M.  [1R-[1α,2β(Z),3β,4α]]-7-[3-[(Hexyloxy)methyl]-7-oxabicyclo[2.2.1]hept-2-yl]-2,2-dimethyl-5-heptenoic acid, 1-(1-oxopropoxy)propyl ester A mixture of Part L acid (300 mg, 0.818 mmole) triethylamine (0.65 ml, 4.64 mmole), α-chloro-n-propyl propionate (388 mg, 2.57 mmole) and sodium iodide (260 mg, 1.73 mmole) in 2.5 ml of dry dimethylformamide was heated to 70 (oil bath temperature) under nitrogen for 6 hours. The mixture was cooled to room temperature, poured into water, saturated with sodium chloride and extracted with ethyl ether (3×100 ml). The combined ether extracts were washed with saturated NaHCO$_3$ solution, dried over anhydrous MgSO$_4$ and evaporated in vacuo to give an oil. This was flash-chromatographed on a 200 g silica gel (LPS-1) column, eluting with ethyl acetate-hexane (1:9) to give 255 mg (64.9%) of a tlc-homogeneous and analytical specimen of title compound, $[\alpha]_D^{23}+2.2°$ (c, 1.02; CHCl$_3$) with consistent mass, IR (1757 cm$^{-1}$, strong C=O), H$^1$-NMR and C$^{13}$-NMR spectral data.

Anal. Calcd. for C$_{28}$H$_{48}$O$_6$: C, 69.96; H, 10.07. Found: C, 69.92; H, 9.93.

H$^1$-NMR Spectrum (CDCl$_3$, FX-270): δ 0.88 (t, 3H, J=~8.0, H$_{21}$); 0.97 (t, 3H, J=~8, H$_{26}$); 1.15 (t, 3H, J=~8, H$_{29}$); 1.20 (s, 6H, H$_{22}$+H$_{23}$); 2.34 (q, 2H, J=~8, H$_{28}$); 3.38 (m, 4H, H$_{14}$+H$_{16}$); 4.18 (d, 1H, J=~4.0, H$_9$ of 5,6 cis double bond isomer, 85.7%); 4.23 (d, H$_9$ of trans double bond isomer, 14.3%); 4.40 (d, 1H, J=~4.0, H$_{12}$); 5.33 (m, 2H, H$_5$+H$_6$); 6.74 (t, 1H, J=~4.0, H$_{24}$).

EXAMPLE 44

[1R-[1α,2β(Z),3β,4α]]-7-[3-[(Hexyloxy)methyl]-7-oxabicyclo[2.2.1]hept-2-yl]-2,2-dimethyl-5-heptenoic acid, 1-(2,2-dimethyl-1-oxopropoxy)propyl ester A. α-Chloropropyl trimethylacetate To a stirred solution of pivaloyl chloride (17.07 ml, 138.5 mmole) and zinc chloride (35 mg) in 50 ml of dry dichloromethane at 0° (ice bath) under nitrogen was added a solution of propionaldehyde (10 ml, 138.6 mmole) in 35 ml of dry dichloromethane portionwise (3 ml every 3 minutes). After the addition was complete, the solution was gradually warmed up to room temperature and stirred for 2 hours. The resulting solution was poured into a 10% sodium carbonate solution and extracted with pentane. The pentane extract was washed with brine, dried over anhydrous CaCl$_2$, filtered and distilled. After the pentane distilled off, the residue was distilled in vacuum (5 mm Hg) to give 14 g of the title compound, b.p. 55°–60°, with consistent spectral data (H$^1$-NMR and C$^{13}$-NMR).

B. [1R-[1α,2β(Z),3β,4α]]-7-[3-[(Hexyloxy)methyl]-7-oxabicyclo[2.2.1]hept-2-yl]-2,2-dimethyl-5-heptenoic acid, 3-(2,2-dimethyl-1-oxopropoxy)propyl ester A stirred mixture of Example 43 Part L acid (200 mg, 0.545 mmole), triethylamine (0.64 ml, 3.30 mmole), α-chloropropyl trimethylacetate (488 mg, 3.27 mmole) and sodium iodide (188 mg, 1.25 mmole) in 3 ml of dry dimethylformamide was heated to 90° (oil bath temperature) under nitrogen for 6 hours. The mixture was cooled to room temperature, poured into water, saturated with sodium chloride and extracted with ethyl ether (3×75 ml). The ether extracts were combined and washed with a saturated NaHCO$_3$ solution and brine, dried over anhydrous MgSO$_4$ and evaporated in vacuo to give an oil. This was flash-chromatographed on a 200 g silica gel (LPS-1) column, eluting with ethyl acetate-hexane (5:95) to give, after drying in vacuo, 245 mg (88.6%) of a tlc-homogeneous and analytical specimen of title compound, $[\alpha]_D^{23}+2.1°$ (c, 1.49, CHCl$_3$) with consistent mass, IR (1755 cm$^{-1}$, strong C=O), H$^1$-NMR and C$^{13}$-NMR spectral data (less than 2% of the 5,6-trans double bond isomer was present by the H$^1$-NMR spectrum).

Anal. Calcd. for C$_{30}$H$_{52}$O$_6$: C, 70.82; H, 10.30%. Found: C, 70.80; H, 10.21%.

H$^1$-NMR Spectrum (CDCl$_3$, FX-270): δ 0.90 (t, 3H, J=~8.0, H$_{21}$); 0.98 (t, 3H, J=~8.0, H$_{26}$); 1.20 (s, 9H, H$_{28}$+H$_{29}$+H$_{30}$); 1.24 (s, 6H, H$_{22}$+H$_{23}$); 2.01 (m, 4H, H$_4$+H$_7$); 3.36 (m, 4H, H$_{14}$+H$_{16}$); 4.18 (d, 1H, J=~4.0, H$_9$); 4.43 (d, 1H, J=~4.0, H$_{12}$); 5.34 (m, 2H, H$_5$+H$_6$); 6.72 (t, 2H, J=~6.0, H$_2$).

EXAMPLE 45

[1R-[1α,2β(5Z),3β,4α]]-7-[3-[(Hexyloxy)methyl]-7-oxabicyclo[2.2.1]hept-2-yl]-3,3-dimethyl-6-octen-2-one A. [1R-[1α,2β(5Z),3β,4α]]-7-[3-[(Hexyloxy)methyl]-7-oxabicyclo[2.2.1]hept-2-yl]-3,3-dimethyl-1-diazo-6-octen-3-one A solution of [1R-[1α,2β(Z),3β,4α]]-7-[3-[(hexyloxy)methyl]-7-oxabicyclo[2.2.1]hept-2-yl]-2,2-dimethyl-5-heptenoic acid (prepared as described in Example 43 Part L) (500 mg, 1.48 mmole) in dry benzene (10 ml) was mixed with oxalyl chloride (0.87 ml, 10 mmole). After 2 hours, the solution was evaporated in vacuo. The residual oil was diluted with dry ether (15 ml) and an approximately three-fold excess of a dry solution of diazomethane in ether was added. Evolution of nitrogen subsided in about 30 minutes. The solution was then concentrated and was dried in vacuo to afford the title diazoketone as an oil (520 mg, 96.8%). A tlc examination (silica gel; Et$_2$O-hexane, 3:2) showed the absence of the starting acid and the presence of mainly the diazoketone. The IR spectrum showed strong peaks at 2108 (N=N) and 1648 (c=o) cm$^{-1}$ characteristic of alpha-diazoketones. This material was used in the next step without further characterization.

B. [1R-[1α,2β(5Z),3β,4α]]-7-[3-[(Hexyloxy)methyl]-7-oxabicyclo[2.2.1]hept-2-yl]-1-chloro-3,3-dimethyl-6-octen-3-one A solution of the Part A diazoketone (450 mg, 1.15 mmole) in dry Et$_2$O (30 ml) was cooled and stirred in an ice bath and a slow stream of dry HCl gas bubbled until the starting material disappeared (about 5 minutes). It was then diluted with ether, warmed to room temperature and washed with water, a dilute NaHCO$_3$ solution and water, dried (MgSO$_4$ anhydrous) and evaporated to afford title compound as an oil (436 mg, 94.7%). This contained only trace amounts of two impurities (tlc) and was used in the next step without further purification [MS, (M+H)$^+$=399; H$^1$-NMR spectrum 9FX-270, (CDCl$_3$): δ 4.05 (s, 2H, CH$_2$Cl).

C. [1R-[1α,2β(5Z),3β,4α]]-7-[3-[(Hexyloxy)methyl]-7-oxabicyclo[2.2.1]hept-2-yl]-3,3-dimethyl-6-octen-2-one A solution of Part B compound (430 mg, 1.08 mmole) in glacial acetic acid (20 ml) was stirred with NaI (400 mg) and Zn dust (1.5 g) for 1.0 hour. The mixture was then diluted with ether (100 ml) and filtered through a bed of Celite. The solids in the funnel were washed with small amounts of ether. The combined washings and filtrate were washed with water, a dilute NaHCO$_3$ solution and water, dried (MgSO$_4$ anhydrous) and evaporated to afford the crude product as an oil (385 mg). This was subjected to flash chromatography on a column of silica gel (LPS-1) eluting with Et$_2$O-hexane (15:85) to isolate, after drying in vacuo, the analytical specimen of title compound, as an oil (362 mg, 92%), (about 9% of 5,6-trans double bond isomer was present (H$^1$-NMR spectrum)).

$[\alpha]_D^{23}=(+)1.14°$ (c, 5.8; CHCl$_3$) with consistent mass, IR (1706 cm$^{-1}$, strong, C=O), H$^1$-NMR and C$^{13}$-NMR spectral data.

Anal. Calcd. for C$_{23}$H$_{40}$O$_3$: C, 75.77; H, 11.05. Found: C, 75.72; H, 11.02.

H$^1$-NMR spectrum (FX-270, CDCl$_3$): δ 0.90 (t, 3H, J=~7.0, H$_{21}$); 1.17 (s, 6H, —, H$_{22}$+H$_{23}$); 2.13 (s, —, —, H$_{24}$ of 5,6-trans isomer); 2.15 (s, —, —, H$_{24}$ of 5,6-cis isomer); 3.37 (m, 4H, —, H$_{14}$+H$_{16}$); 4.17 (d, 0.9H, J=~4.0, H$_9$ of 5,6-cis isomer); 4.22 (d, 0.1H, J=~4.0; H$_9$ of 5,6-trans isomer); 4.35 (d, 0.1H, J=~4.0, H$_{12}$ of 5,6-trans isomer); 4.50 (d, 0.9H, J=~4.0, H$_{12}$ of 5,6-cis isomer); 5.33 (m, 2H, —, H$_5$+H$_6$).

EXAMPLE 46 TO 51

Following the procedure of Example 43 except substituting for hexyl mesylate, the compound shown in Column A of Table I set out below, and substituting for α-chloro-n-propyl propionate, the compound shown in Column B, the product shown in Column C is obtained.

TABLE I

| | Column A | Column B | Column C | | | |
|---|---|---|---|---|---|---|
| Ex. No. | R$^1$ | R$^4$ R$^5$ R$^6$ | R$^1$ | R$^4$ | R$^5$ | R$^6$ |
| 46. | C$_5$H$_{11}$ | H H CH$_3$ | as per Column A | as per Column B | | |
| 47. | C$_9$H$_{19}$ | CH$_3$ C$_2$H$_5$ C$_3$H$_7$ | | | | |
| 48. | C$_6$H$_4$CH$_2$ | H C$_6$H$_5$ CH$_3$O | | | | |
| 49. | C$_6$H$_5$ | C$_6$H$_4$CH$_2$ H C$_2$H$_5$O | | | | |
| 50. | 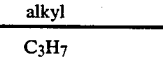 | C$_6$H$_5$ CH$_3$ C$_2$H$_5$ | | | | |
| 51. | 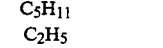—CH$_3$ | CH$_3$ CH$_3$ CH$_3$ | | | | |

Column A: 

Column B: 

Column C: 

EXAMPLE 52 TO 57

Following the procedure of Example 43 and 45 except substituting for hexyl mesylate, the compound shown in Column A of Table II set out below, and substituting for diazomethane, the diazo alkane shown in Column B, the product shown in Column C is obtained.

TABLE II

Column A: 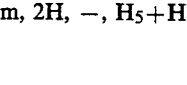

Column B: AlkylCOOH

Column C: 

| Ex. No. | R$^1$ | alkyl | R$^1$ | alkyl |
|---|---|---|---|---|
| 52. | C$_4$H$_9$ | C$_3$H$_7$ | as per Column A | as per Column B |
| 53. | C$_8$H$_{17}$ | C$_4$H$_9$ | | |
| 54. | C$_6$H$_4$CH$_2$ | C$_5$H$_{11}$ | | |
| 55. | C$_6$H$_5$ | C$_2$H$_5$ | | |
| 56. |  | CH$_3$ | | |

TABLE II-continued

| | Column A | Column B | Column C 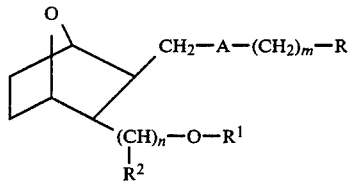 | |
|---|---|---|---|---|
| | $R^1-\overset{\overset{O}{\|}}{\underset{\underset{O}{\|}}{S}}-CH_3$ | AlkylCOOH | | |
| Ex. No. | $R^1$ | alkyl | $R^1$ | alkyl |
| 57. | 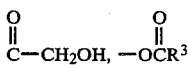—CH$_2$ | C$_6$H$_{13}$ | } | } |

What is claimed is:
1. A compound having the structural formula

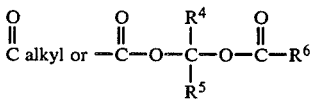

and including all stereoisomers thereof, wherein A is
—CH=CH— or —(CH$_2$)$_2$—;
m is 1 to 8; n is 1 to 4;
R is OH, $$\overset{O}{\underset{\|}{C}}-CH_2OH, \quad -\overset{O}{\underset{\|}{O}}CR^3$$

(wherein R$^3$ is lower alkyl, aryl, arylalkyl or lower alkylamino), $$\overset{O}{\underset{\|}{C}} \text{ alkyl or } -\overset{O}{\underset{\|}{C}}-O-\overset{R^4}{\underset{R^5}{C}}-O-\overset{O}{\underset{\|}{C}}-R^6$$

(wherein R$^4$ and R$^5$ may be the same or different and are H, alkyl, aryl or arylalkyl and R$^6$ is alkyl, O-alkyl or aryl); R$^1$ is lower alkyl, aryl, aralkyl, cycloalkyl or cycloalkylalkyl; and R$^2$ is H or lower alkyl, but where R$^2$ is lower alkyl, n is 1, wherein the term lower alkyl or alkyl by itself or as part of another group contains 1 to 12 carbons and is unsubstituted or substituted with halo, trifluoromethyl, alkoxy, alkylthio, alkylamino, haloaryl, cycloalkyl or alkylcycloalkyl;
the term aryl by itself or as part of another group contains 6 to 10 carbons and is unsubstituted or substituted with lower alkyl, halogen or lower alkoxy;
the term cycloalkyl by itself or as part of another group contains 3 to 12 carbons and is unsubstituted or substituted with 1 or 2 halogens, 1 or 2 lower alkyl groups and/or 1 or 2 lower alkoxy groups; and
(CH$_2$)$_m$ can contain one or more lower alkyl substituents.

2. The compound as defined in claim 1 wherein A is —CH=CH—.
3. The compound as defined in claim 1 wherein R$^2$ is H.
4. The compound as defined in claim 1 wherein n is 1.
5. The compound as defined in claim 1 wherein A is (CH$_2$)$_2$ and R is OH.
6. The compound as defined in claim 1 wherein n is 1, R is OH and R$^1$ is lower alkyl, phenyl or cycloalkyl.
7. The compound as defined in claim 1 wherein n is 1, R is $$\overset{O}{\underset{\|}{O}}\text{Calkyl}$$

and R$^1$ is lower alkyl, phenyl or cycloalkyl.
8. The compound as defined in claim 1 wherein n is 1, R is $$\overset{O}{\underset{\|}{C}}CH_2OH$$

and R$^1$ is lower alkyl, phenyl or cycloalkyl.
9. The compound as defined in claim 1 wherein R is $$\overset{O}{\underset{\|}{C}}\text{alkyl}.$$

10. The compound as defined in claim 1 wherein R is

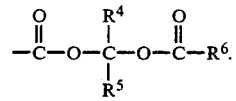

11. The compound as defined in claim 1 having the name [1α,2β,3β,4α]-4-[3-[(hexyloxy)methyl]-7-oxabicyclo[2.2.1]hept-2-yl]butanol, including all stereoisomers thereof.
12. The compound as defined in claim 1 having the name [1R-[1α,2β(5Z),3β,4α]]-7-[3-[(hexyloxy)methyl]-7-oxabicyclo[2.2.1]hept-2-yl]-2,2-dimethyl-5-hepten-1-ol including all stereoisomers thereof.
13. The compound as defined in claim 1 having the name [1R-[1α,2β(5Z),3β,4α]]-7-[3-[(hexyloxy)methyl]-7-oxabicyclo[2.2.1]hept-2-yl]-2,2-dimethyl-5-hepten-1- ol or its acetate ester, including all stereoisomers thereof.

14. The compound as defined in claim 1 having the name 1R-[1α,2β,3β,4α]]-7-[3-[(hexyloxy)methyl]-7-oxabicyclo[2.2.1]hept-2-yl]-2,2-dimethyl-1-heptanol, including all stereoisomers thereof.

15. The compound as defined in claim 1 having the name [1R-[1α,2β(2±,5Z),3β,4α]]-7-[(3-hexyloxy)methyl]-7-oxabicyclo[2.2.1]hept-2-yl]-2-methyl-5-heptenol, including all stereoisomers thereof.

16. The compound as defined in claim 1 having the name [1R-[1α,2β(5Z),3β,4α]]-7-[3-[(hexyloxy)-methyl]-7-oxabicyclo[2.2.1]hept-2-yl]-5-heptenol, including all stereisomers thereof.

17. The compound as defined in claim 1 having the name [1R-[1α,2β(5Z),3β,4α]]-7-[(hexyloxy)methyl]-7-oxabicyclo[2.2.1]hept-2-yl]-1-hydroxy-6-octen-2-one, including all stereoisomers thereof.

18. The compound as defined in claim 1 having the name [1R-[1α,2β(Z),3β,4α]]-7-[3[hexyloxy)methyl]-7-oxabicyclo[2.2.1]hept-2-yl]-2,2-dimethyl-5-heptenoic acid, 1-(1-oxopropoxy)propyl ester, including all stereoisomers thereof.

19. The compound as defined in claim 1 having the name [1R-[1α,2α(Z),3β,4α]]-7-[3[(hexyloxy)methyl]-7-oxabicyclo[2.2.1]hept-2-yl]-2,2-dimethyl-5-heptenoic acid, 1-(2,2-dimethyl-1-oxopropoxy)propyl ester, including all stereoisomers thereof.

20. The compound as defined in claim 1 having the name [1R-[1α,2β(5Z),3β,4α]]-7-[3-[(hexyloxy)methyl]-7-oxabicyclo[2.2.1]hept-2-yl]-3,3-dimethyl-6-octen-2-one, including all stereoisomers thereof.

21. A compound having the name [1R-[1α,2β(5Z),3β,4α]]-7-[3-[(hexyloxy)methyl]-7-oxabicyclo[2.2.1]hept-2-yl]-2,2-dimethyl-5-heptenol, phenylalanyl ester, including all stereoisomers thereof.

22. A method of inhibiting platelet aggregation and bronchoconstriction, which comprises administering to the circulatory system of a mammalian host an effective amount of a compound as defined in claim 1 or a pharmaceutically acceptable salt thereof.

23. The method as defined in claim 22 wherein said compound is administered in an amount within the range of from about 1 to about 100 mg/kg.

24. A composition for inhibiting platelet aggregation and bronchoconstriction comprising an effective amount of a compound as defined in claim 1 or a pharmaceutically acceptable salt thereof, and a pharmaceutically acceptable carrier thereof.

25. A method of inhibiting platelet aggregation, inhibiting bronchoconstriction, treating inflammation or relieving pain which comprises administering to a mammalian host an effective amount of a compound as defined in claim 1 or a pharmaceutically acceptable salt thereof.

* * * * *

UNITED STATES PATENT AND TRADEMARK OFFICE
CERTIFICATE OF CORRECTION

PATENT NO. : 4,588,743

DATED : May 13, 1986

INVENTOR(S) : Martin F. Haslanger et al.

It is certified that error appears in the above-identified patent and that said Letters Patent is hereby corrected as shown below:

Column 3, lines 25-29 should read --for $NH_2$ to $-\overset{O}{\underset{\|}{C}}-$ --.

Column 13, line 48, "XVI'" should read --XV'--.
Column 15, line 60, after "wherein" insert --$(CH_2)_m$ is--.
Column 15, line 66, before "prepared" insert --may be--.
Column 17, line 30, "ay" should read --any--.
Column 27, line 42, "$Et_2$-hexane" should read --$Et_2$O-hexane--.
Column 37, line 51, "-b 2" should read -- -2 --.
Column 39, line 1, "70" should read --70°--.
Column 45, line 25, "1α,2α" should read --1α,2β--.

Signed and Sealed this

Twenty-third Day of December, 1986

Attest:

DONALD J. QUIGG

Attesting Officer

Commissioner of Patents and Trademarks